(12) United States Patent
Nilsson

(10) Patent No.: US 10,583,279 B2
(45) Date of Patent: Mar. 10, 2020

(54) DIALYSIS APPARATUS WITH VERSATILE USER INTERFACE AND METHOD AND COMPUTER PROGRAM THEREFOR

(71) Applicant: GAMBRO LUNDIA AB, Lund (SE)

(72) Inventor: Roger Nilsson, Höör (SE)

(73) Assignee: Gambro Lundia AB, Lund (SE)

(*) Notice: Subject to any disclaimer, the term of this patent is extended or adjusted under 35 U.S.C. 154(b) by 198 days.

(21) Appl. No.: 15/035,546

(22) PCT Filed: Nov. 11, 2014

(86) PCT No.: PCT/EP2014/074280
§ 371 (c)(1),
(2) Date: May 10, 2016

(87) PCT Pub. No.: WO2015/071265
PCT Pub. Date: May 21, 2015

(65) Prior Publication Data
US 2016/0292377 A1    Oct. 6, 2016

(30) Foreign Application Priority Data

Nov. 18, 2013 (SE) ..................... 1351362

(51) Int. Cl.
*A61M 37/00* (2006.01)
*A61M 5/168* (2006.01)
(Continued)

(52) U.S. Cl.
CPC .......... *A61M 37/00* (2013.01); *A61M 1/1601* (2014.02); *A61M 5/168* (2013.01);
(Continued)

(58) Field of Classification Search
CPC .... G06F 19/3418; G16H 40/63; G05B 15/02; A61M 1/1601; A61M 2205/502; A61M 2205/505

See application file for complete search history.

(56) References Cited

U.S. PATENT DOCUMENTS 5,609,770 A   3/1997   Zimmerman et al.
5,795,317 A   8/1998   Brierton et al.
(Continued)

FOREIGN PATENT DOCUMENTS

CN    104321772 A1    1/2015
WO    2010027437       3/2010
(Continued)

OTHER PUBLICATIONS

Search Report for International Patent Application PCT/EP2014/074280 dated Mar. 31, 2015 (3 pages).
(Continued)

*Primary Examiner* — Ajay Ojha
(74) *Attorney, Agent, or Firm* — K&L Gates LLP

(57) ABSTRACT

There is provided an apparatus for performing operation steps of a dialysis process. The apparatus comprises a process controller for controlling the apparatus, monitor process progress of the dialysis process and monitor sensor inputs from sensors of the apparatus, and a user interface, UI, comprising a display, an input device and a UI controller. The UI controller is connected to enable presentation of graphical data on the display. The UI controller is connected to enable user interaction with the graphical data and connected to exchange information with the process controller. The UI controller is configured to represent each of the operation steps by step items. The amount of operation guidance information of an operation step item is selectable by the operator during the dialysis process. A method and computer program are also disclosed.

17 Claims, 12 Drawing Sheets

(51) Int. Cl.
*G16H 40/63* (2018.01)
*A61M 1/16* (2006.01)
*G05B 15/02* (2006.01)
*G06F 19/00* (2018.01)
*A61M 5/145* (2006.01)

(52) U.S. Cl.
CPC ......... *G05B 15/02* (2013.01); *G06F 19/3418* (2013.01); *G16H 40/63* (2018.01); *A61M 5/145* (2013.01); *A61M 2205/502* (2013.01); *A61M 2205/505* (2013.01)

(56) References Cited

U.S. PATENT DOCUMENTS

| | | | |
|---|---|---|---|
| 2001/0016821 A1* | 8/2001 | DeBusk | G06F 19/324 705/2 |
| 2002/0085952 A1 | 7/2002 | Ellingboe et al. | |
| 2008/0176210 A1 | 7/2008 | Moll et al. | |
| 2011/0098635 A1* | 4/2011 | Helmore | A61M 1/28 604/29 |
| 2012/0078658 A1* | 3/2012 | Hilgers | A61M 1/16 705/2 |
| 2012/0109037 A1 | 5/2012 | Ellingboe et al. | |
| 2012/0138533 A1 | 6/2012 | Curtis et al. | |
| 2012/0238851 A1* | 9/2012 | Kamen | A61M 5/14244 600/365 |
| 2013/0037485 A1 | 2/2013 | Wilt et al. | |
| 2013/0205407 A1 | 8/2013 | Golshenas | |
| 2015/0355790 A1* | 12/2015 | O'Mahony | G06F 19/3406 715/771 |

FOREIGN PATENT DOCUMENTS

| | | |
|---|---|---|
| WO | 2011144747 | 11/2011 |
| WO | 2014033119 | 3/2014 |

OTHER PUBLICATIONS

Written Opinion for International Patent Application PCT/EP2014/074280 dated Mar. 31, 2015 (15 pages).

* cited by examiner

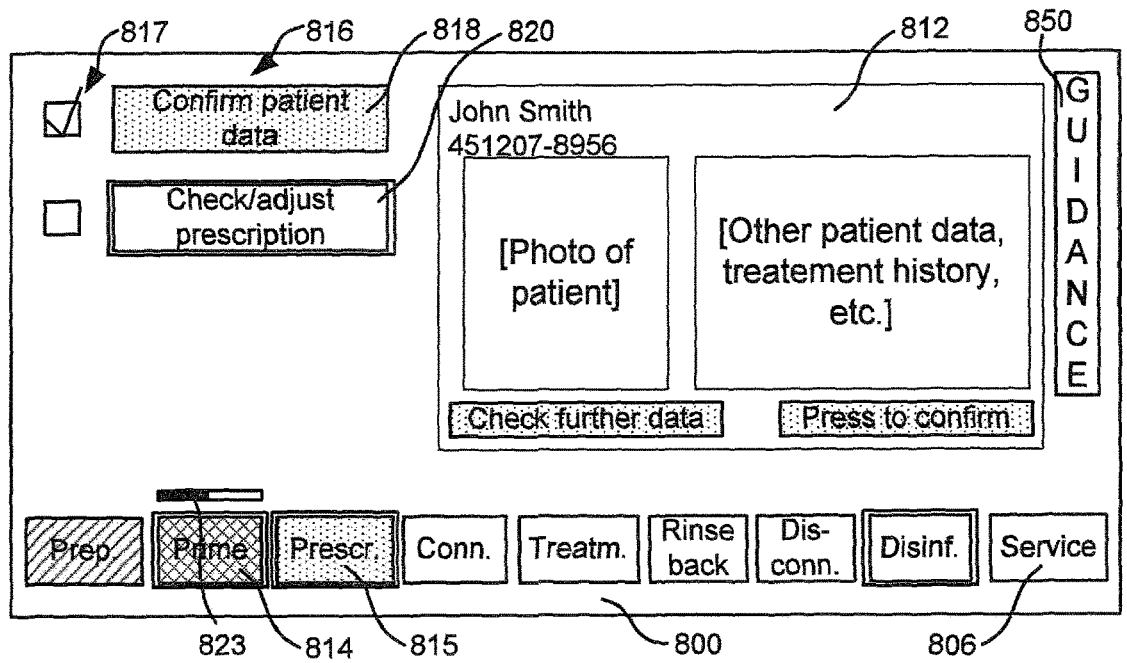
FIG. 16
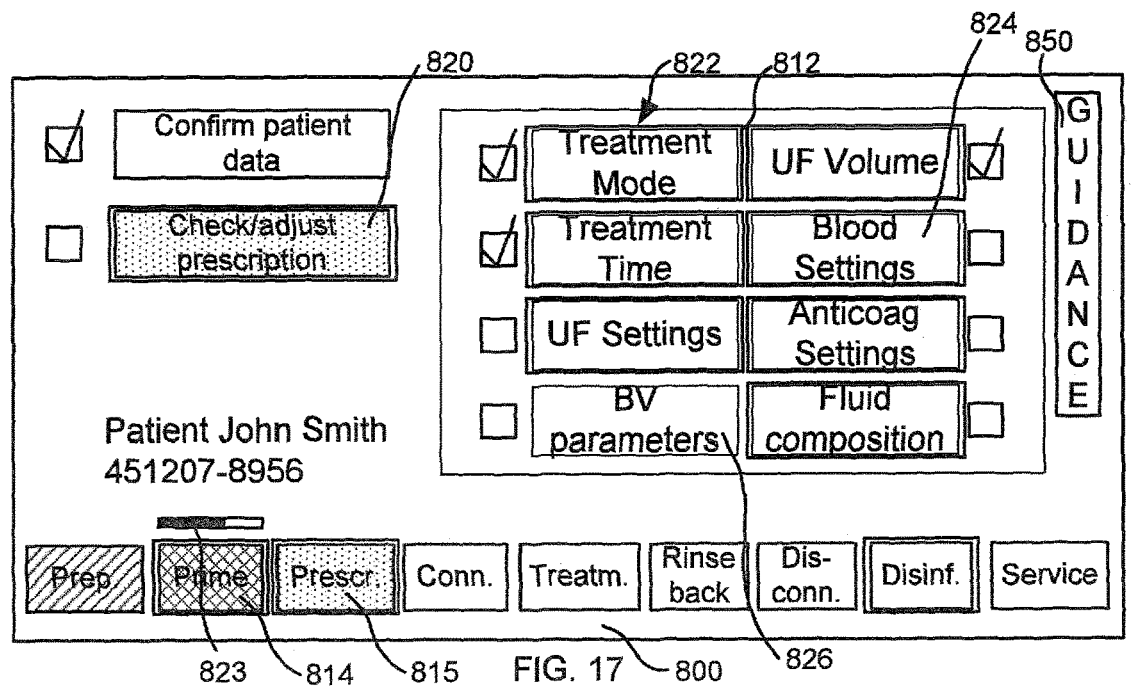
FIG. 17
FIG. 18

DIALYSIS APPARATUS WITH VERSATILE USER INTERFACE AND METHOD AND COMPUTER PROGRAM THEREFOR

PRIORITY CLAIM

The present application is a National Phase of International Application No. PCT/EP2014/074280, filed on Nov. 11, 2014, which claims priority to Swedish Patent Application No. 1351362-7, filed Nov. 18, 2013, the entire contents of each of which are incorporated herein by reference and relied upon.

TECHNICAL FIELD

The present invention generally relates to an apparatus for performing a dialysis process, a method for such an apparatus, and a computer program for implementing the method. In particular, the invention relates to an improved user interface approach for dialysis apparatuses.

BACKGROUND

Apparatuses for dialysis process, e.g. dialysis apparatuses and possible attached apparatuses such as water preparation units, treatment substrate and/or fluid supply, medical file systems, etc., normally have a user interface, UI, that is rigidly connected to the hardware of the apparatus. The user will thus need to be trained on that particular apparatus, and the apparatus will be limited in what context it can be used.

US 2008/0176210 A1 discloses a dialysis apparatus having a program library comprising several data sets, each corresponding to a functional process. The programs stored in the program library include configuration data sets, user wishes and further information items. For establishing the data sets, a computer receives a model of the dialysis apparatus which is adapted to have parameters entered, and will simulate a functional process with these parameters. Subsequent to such a functional process, the respective data set will be stored in the program library. A larger number of data sets and thus functional processes can be at disposal of an experienced user than to an average-skilled nurse. The latter kind of users will be given a restricted range of options. A specific and optimised treatment process can thus be used without entailing a risk of misguided operation by normal health-care personnel since the handling of the blood treatment apparatus is reduced to those operating steps which are absolutely required. This provides for some degree of flexibility, but still suffers from the static behaviour of the apparatus once a data set has been selected prior the treatment, and the limitation to pre-programmed data sets, which in practice will not fit optimally to each combination of treatment and user.

It is therefore a desire to provide an enhanced UI, which in turn will provide a more versatile apparatus for dialysis.

SUMMARY

An object of the invention is to at least alleviate the above stated problem. The present invention is based on the understanding that ability to provide the correct amount of information to a user will make handling more efficient to all users, irrespective if they are highly trained and need only very little information or just uses an apparatus now and then and requires a lot more information, including some guidance.

According to a first aspect, there is provided an apparatus for performing a plurality of operation steps of a dialysis process. The apparatus comprises a process controller for controlling the apparatus to perform the operation steps of the dialysis process, monitor process progress of the dialysis process and monitor sensor inputs of sensors of the apparatus, and a user interface, UI, comprising a display, an input device and a UI controller. The UI controller is connected to enable presentation of graphical data on the display. The UI controller is connected to enable user interaction with the graphical data and connected to exchange information with the process controller. The exchanged information is based on the user interaction of the user interface and monitoring of process progress of the dialysis process and sensor inputs of sensors of the apparatus monitored by the process controller. The UI controller is configured to represent each of the operation steps by one or more operation step items. Each graphical item is suitable to be presented on said display. The amount of operation guidance information of an operation step item is selectable by the operator during the dialysis process to be in one of at least a first and a second state. The second state provides a larger amount of guidance than the first state.

The dialysis process in this context may also comprise processes, e.g. filtration processes, such as ultrafiltration, slow continuous ultrafiltration, hemodiafiltration, hemofiltration, hemoperfusion, etc., where dialysis per se is not performed.

One or more operation step items of said operation step items may be recommended by the UI controller to be performed next, and may be displayed with an indicator representing the recommendation, when in a state other than the first state.

The UI controller may be arranged to disable selection of the first state based on a determined skill level of the operator to be lower than a threshold.

At least one of the operation step items may comprise operation substep items that represent substeps of the at least one operation step by at least one of operation guidance, parameter setting and status information, and wherein the UI controller may be arranged to enable displaying of the operation substep items upon displaying of the corresponding operation step item when in another state than the first state. The UI controller may be arranged to enable the displaying of a subset of the operation substep items upon displaying of the corresponding operation step item associated with the subset of operation substep items based on an input from the operator, wherein such enabling based on input from the operator may override any corresponding disabling of the displaying of the operation substep items by the UI controller when in another state than the first state. The UI controller may be arranged to disable the displaying of a subset of the operation substep items upon displaying of the corresponding operation step item associated with the subset of operation substep items based on an input from the operator when in the first state. The at least a first and a second state may comprise a third state, wherein the third state may provide a larger amount of guidance than the second state, and at least one of the operation substep items may comprise operation substep items on a further level of detail that represent operation substeps on a further level of detail of the at least one substep by at least one of operation guidance, parameter setting and status information, and wherein the UI controller may be arranged to enable displaying of the operation substep items on a further level of detail upon displaying of the corresponding operation substep item when in the third state. The UI controller may be arranged to enable the displaying of the operation substep items on a further level of detail upon displaying of the corresponding operation substep item based on an input from the operator, wherein such enabling based on input from the operator may override any corresponding disabling of the displaying of the operation substep items on a further level of detail by the UI controller when in another state than the third state. The UI controller may be arranged to disable the displaying of a subset of the operation substep items on a further level of detail upon displaying of the corresponding operation substep item associated with the subset of the operation substep items on a further level of detail based on an input from the operator when in the third state.

A larger amount of guidance may include more operation step items for an operation step than a lesser amount of guidance.

According to a second aspect, there is provided a method of an apparatus for a dialysis process comprising a plurality of operation steps. The method comprises representing each of the operation steps as an operation step item being a graphical item suitable to be presented on a display of a user interface, UI, enabling one or more of said operation step items of operation steps to be displayed through the UI, and selection among those items through an input device of the UI, and receiving an input from an operator, and selecting during the dialysis process an amount of operation guidance information of an operation step item based on the input to be in one of at least a first and a second state. The second state provides a larger amount of guidance than the first state.

The method may comprise displaying one or more operation step items of said operation step items recommended to be performed next with an indicator representing the recommendation when in another state than the first state.

The method may comprise disabling selection of the first state based on a determined skill level of the operator to be below a threshold.

At least one of the operation step items may comprise operation substep items that represent operation substeps of the at least one operation step by at least one of operation guidance, parameter setting and status information, and the method may comprise enabling displaying of the operation substep items upon displaying of the corresponding operation step item when in another state than the first state. The method may comprise receiving an input from the operator, and enabling the displaying of a subset of the operation substep items upon displaying of the corresponding operation step item associated with the subset of the operation substep items based on the input when in the second state, wherein such enabling based on input from the operator may override any corresponding disabling of the displaying of the operation substep items by the UI controller when in the first state. The method may comprise receiving an input from the operator, and disabling the displaying of a subset of the operation substep items upon displaying of the corresponding operation step item associated with the subset of the operation substep items based on the input when in another state than the first state. The at least a first and a second state may comprise a third state, wherein the third state provides a larger amount of guidance than the second state, and the operation substep items comprises operation substep items on a further level of detail that represent substeps on a further level of detail of the at least one substep by at least one of operation guidance, parameter setting and status information, and the method may comprise enabling displaying of the operation substep items on a further level of detail upon displaying of the corresponding operation substep item when in the third state. The method may comprise receiving an input from the operator, and enabling the displaying of a subset of the operation substep items on a further level of detail upon displaying of the corresponding operation substep item associated with the subset of the operation substep items on a further level of detail based on the input from the operator, wherein such enabling based on input from the operator may override any corresponding disabling of the displaying of the operation substep items on a further level of detail by the UI controller when in another state than the third state. The method may comprise receiving an input from the operator, and disabling the displaying of a subset of the operation substep items on a further level of detail upon displaying of the corresponding operation substep item associated with the subset of the operation substep items on a further level of detail based on the input when in the third state.

A larger amount of guidance may include more operation step items for an operation step than a lesser amount of guidance.

According to a third aspect, there is provided a computer program comprising computer-executable program code which when executed by a processor of an apparatus for a dialysis process causes the apparatus to perform the method according to the second aspect.

Other objectives, features and advantages of the present invention will appear from the following detailed disclosure, from the attached dependent claims as well as from the drawings. Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated. Furthermore, as will be understood by a reader skilled within the field of technology, the multitude of features demonstrated by the disclosed examples of apparatuses, methods and computer programs, may be combined or configured to be used together with other of those features although not explicitly demonstrated as a particular example. The skilled reader will also recognise the relations between the apparatus, method and computer program examples and is encouraged to contemplate the principles of the features irrespective of whether the given example is an apparatus, method or computer program.

BRIEF DESCRIPTION OF THE DRAWINGS

The above, as well as additional objects, features and advantages of the present invention, will be better understood through the following illustrative and non-limiting detailed description of embodiments of the present invention, with reference to the appended drawings.

FIGS. 8 to 21 illustrate a user interface example according to a first user interface setting.

DETAILED DESCRIPTION

Figure 1:
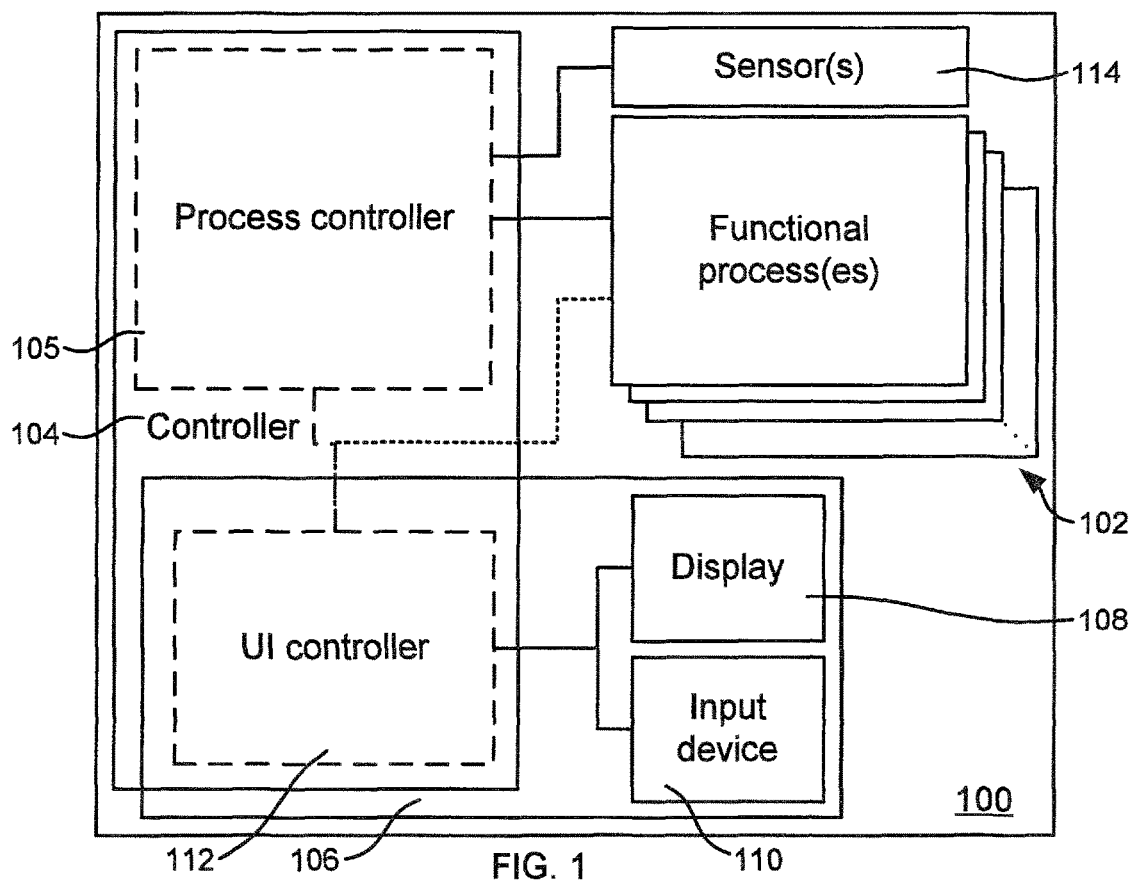
FIG. 1 is a block diagram schematically illustrating an apparatus for a dialysis process.

FIG. 1 is a block diagram schematically illustrating an apparatus 100 for a dialysis process. The dialysis process is performed by one or more functional processes 102, which may be separate units within the apparatus 100, functionally separate tasks performed by the same unit within the apparatus 100, or two or more units within the apparatus 100 jointly performing a functional process. Such a functional process 102 may be water treatment for the dialysis treatment or preparation of dialysis fluid, rinsing mechanism, extracorporeal blood circuit mechanism, etc. A controller 104 of the apparatus controls the operation of the functional processes; thus, the process controller 104 may be a joint controller, a multitude of local controllers, or a hierarchy of controllers working together. The controller 104 may comprise a process controller 105 which may be a separate controller, but may as well be a functional part of the controller structure of the apparatus 100 as a whole. The controller 104 or process controller 105, depending on the configuration, monitors inputs from one or more sensors 114 of the apparatus, such as pressure sensors, temperature sensors, air sensors or (mechanical) position sensors, etc. After this brief description of feasible structures of an apparatus for dialysis, it is already possible to understand that a user, i.e. an operator, such as a nurse, technician or other care personnel, or patient, e.g. at home treatment, is not capable of knowing all the details of different units and/or functional processes of the apparatus 100. Instead, a user interface, UI, 106 is provided, and the aim is to make the UI 106 as convenient to use for the user as possible. The UI 106 comprises an output device such as a display 108 and an input device 110 to be able to interact with the user. The display 108 and the input device 110 may be integrated to a touchscreen. Also other input and output devices may be present such as speaker, signal light indicator, tactile actuator, etc. for output and keyboard or keypad, knob, button, switch, microphone, trackball, touchpad, joystick, mouse, stylo, etc. for input. The UI 106 may comprise a UI controller 112 which controls the features of the UI, as will be further demonstrated below. The UI controller 112 may be a separate controller, but may as well be a functional part of the controller structure of the apparatus 100 as a whole, i.e. of the controller 104.

The UI 106 is connected to the process controller 104 for interchanging of signals, both for providing control data to process controller 104 such that it is able to control the functional processes 102 to make the apparatus 100 perform the desired tasks of the user, and for receiving status and measured data from the controller 104 to be able to adapt behaviour of the UI 106 and/or present relevant data to the user. The UI 106 may also be connected directly to sensors 114 of the apparatus 100, e.g. associated with the functional processes, for the same reasons.

The functional processes 102 and their related units are each arranged to perform their tasks. Simultaneously, the user defines the tasks for the apparatus in maybe a different way. There is therefore a desire to bridge any such differences between the user's viewpoint and the machine's structure. The user's intentions with the treatment by the apparatus are thus not only transferred via the UI to the functional processes, but also in some sense translated. The similar principle applies for data going the other way. Roughly, the user's intentions (and need for information) are here mapped on operation step items which may be presented and/or interacted with through the UI, wherein the operation step items are related to corresponding operation steps, which in turn are actions (and information collection) performed by the functional processes of the apparatus.

A further consideration is the diversity of users, as given by the examples above. What is as convenient as possible to use for one user may not be that for another. Therefore, there is also an aim to provide flexibility of the UI. However, since dialysis is serious matter for the patient, and security in treatment is highest priority, there are several considerations to be made upon providing a flexible UI.

The operation steps may be of different nature. As discussed above, each operation step is configured to provide, through its operation step item, an understandable function for the user. If the operation step is not understandable enough for some users, the operation step may be divided into substeps, which in turn may be divided into further levels of detail.

The operation steps are represented by the operation step items, which may include user understandable information or references to such information, such as operation guidance, parameter setting, status information, etc. From these items, the UI controller 106 may form a structure, e.g. a formal data structure, a state machine, or real-time state structure, of the assignments which form basis for the control of the UI.

In the structure, the operation step items are assigned as selectable if their operation steps are available at the moment. That is, a selectable operation step item is that because it is available for being performed and is not waiting e.g. for another operation step to be completed. Thus, non-selectable operation step items are such since they are not available for being performed. Regarding the completed steps, these are mostly not available, but some may be, e.g. for changing a parameter that already has a value, i.e. may be regarded as completed. On the other hand, a similar completed step with a set parameter may not be available since the parameter needs to be kept constant for other operation steps being in progress. In which case, the information that an operation step is completed is of benefit for the formed structure.

The versatility of the UI is provided since the UI controller is arranged to enable one or more selectable operation step items to be displayed through the UI and enable a user to interact with the displayed operation step items. The user may thus select any of the presented operation step items to start working with since the structure has sorted out the selectable operation step items that are possible to work with.

The UI may of course also display non-selectable operation step items for information, but preferably with some distinction in appearance between the selectable and non-selectable. Also completed operation step items may be displayed, for information if non-selectable and for operation if selectable, preferably with an indication that the operation step items relate to operation steps that are completed.

The amount of displayed UI items may be selected to provide relevant information to the user, while excess information that may confuse the user or obscure the relevant information may be avoided to be displayed. Therefore, the UI controller 112 is configured to represent the operation steps items with an amount of operation guidance information which may vary and which is selectable by the operator during the dialysis process to be in one of at least a state providing less guidance information, i.e. for a user finding more guidance information obscuring, confusing or less efficient at the moment, and a state providing a larger amount of guidance, i.e. for a user desiring more elaborate information at the moment. The switching between the states may be a toggle button, e.g. provided at a touchscreen of the UI, where the user may toggle between the states. There may be further states with further degrees of guidance information or inclination of the guidance information. For example, one state with more guidance information may be inclined towards patient related information, while another state with more guidance can be inclined towards machine related information, and the state providing less guidance information does not provide the guidance in that detail as the "patient" or "machine" inclined extended guidance information states. Further states providing even further information may also be provided. For example can a state providing information from two or more inclinations be provided.

Figure 2:
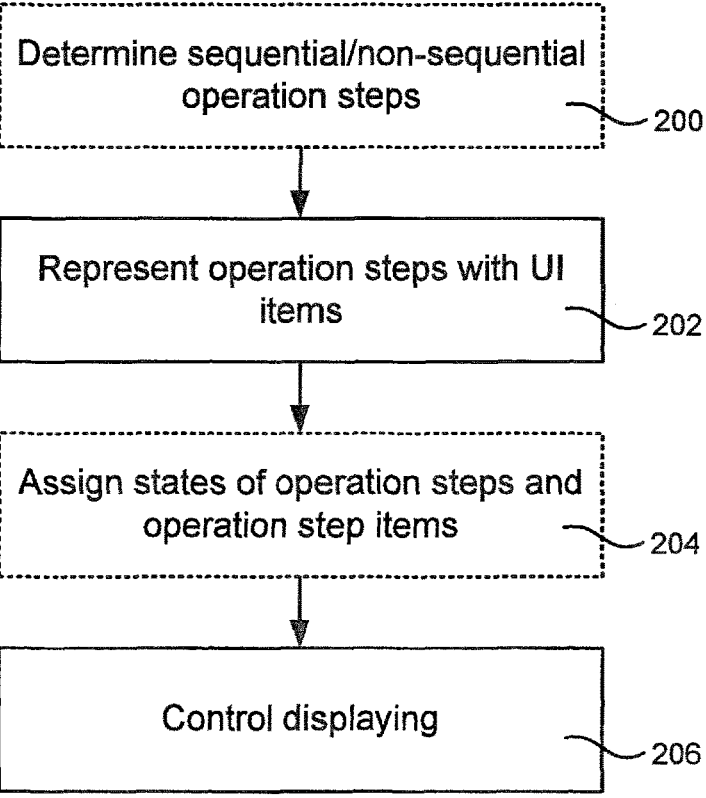
FIG. 2 is a flow chart schematically illustrating a method of an apparatus for dialysis.

FIG. 2 is a flow chart schematically illustrating a method of an apparatus for a dialysis process. The dialysis process is assumed to comprise a plurality of operation steps. By representing 202 each of the operation steps as an operation step item being a graphical item suitable to be presented on a display of a user interface, UI, interaction with the operator on the dialysis process is feasible. The method thus comprises enabling 206 one or more of said operation step items of operation steps to be displayed through the UI, and selection among those items through an input device of the UI, wherein an input from an operator may be received through the UI accordingly. The UI may for example be provided through a touch screen.

Since properties of operation steps may change from treatment to treatment, and also from time to time during a treatment, the method may also comprise determining 200 available operation steps and/or assigning 204 states of operation steps and operation step items. From this, the representing 202 of operation steps with UI items can be made accordingly, and/or displaying 206 of the operation step items may be adapted accordingly.

To provide the versatile UI, the operator is enabled to select, during the dialysis process, an amount of operation guidance information of an operation step item based on the input to be in one of at least a first and a second state, wherein the second state provides a larger amount of guidance than the first state. Thereby the operator may select the appearance of the UI based on desired needs for guidance as discussed above.

Optionally, one or more operation step items of said operation step items can be displayed as recommended to be performed next with an indicator representing the recommendation when in another state than the first state, i.e. to provide further guidance in sense of the order of taking care of the steps.

Also optionally, disabling of selection of the first state may be performed based on a determined skill level of the operator to be below a threshold. The determination of skill can be based on identity of the operator, where e.g. a patient or a less trained operator is forced to receive more guidance, or based on analysis of already performed steps.

For providing further options regarding guidance, at least one of the operation step items may comprise operation substep items that represent operation substeps of the at least one operation step by at least one of operation guidance, parameter setting and status information. Thereby, displaying of the operation substep items upon displaying of the corresponding operation step item when in another state than the first state may be enabled for providing the further guidance. The invoking of the further guidance may be made by receiving an input from the operator, and enabling the displaying of a subset of the operation substep items upon displaying of the corresponding operation step item associated with the subset of the operation substep items based on the input when in the second state, wherein such enabling based on input from the operator overrides any corresponding disabling of the displaying of the operation substep items by the UI controller when in the first state.

An option for reducing the amount of this enhanced guidance when found too elaborate by the operator is to receive an input from the operator, and disable the displaying of a subset of the operation substep items upon displaying of the corresponding operation step item associated with the subset of the operation substep items based on the input when in another state than the first state.

A third state may be provided, wherein the third state provides a larger amount of guidance than the second state, and the operation substep items comprises operation substep items on a further level of detail that represent substeps on a further level of detail of the at least one substep by at least one of operation guidance, parameter setting and status information. The method may thus comprise enabling displaying of the operation substep items on a further level of detail upon displaying of the corresponding operation substep item when in the third state. The method can thus comprise receiving an input from the operator, and enabling the displaying of a subset of the operation substep items on a further level of detail upon displaying of the corresponding operation substep item associated with the subset of the operation substep items on a further level of detail based on the input from the operator. Such enabling based on input from the operator may override any corresponding disabling of the displaying of the operation substep items on a further level of detail by the UI controller when in another state than the third state.

Similarly, this further guidance can be turned off by receiving an input from the operator, and disabling the displaying of a subset of the operation substep items on a further level of detail upon displaying of the corresponding operation substep item associated with the subset of the operation substep items on a further level of detail based on the input when in the third state.

The larger amount of guidance may include more operation step items for an operation step than a lesser amount of guidance. The larger amount of guidance can, additionally or alternatively, comprise further information provided for the respective displayed graphical items.

Figure 3:
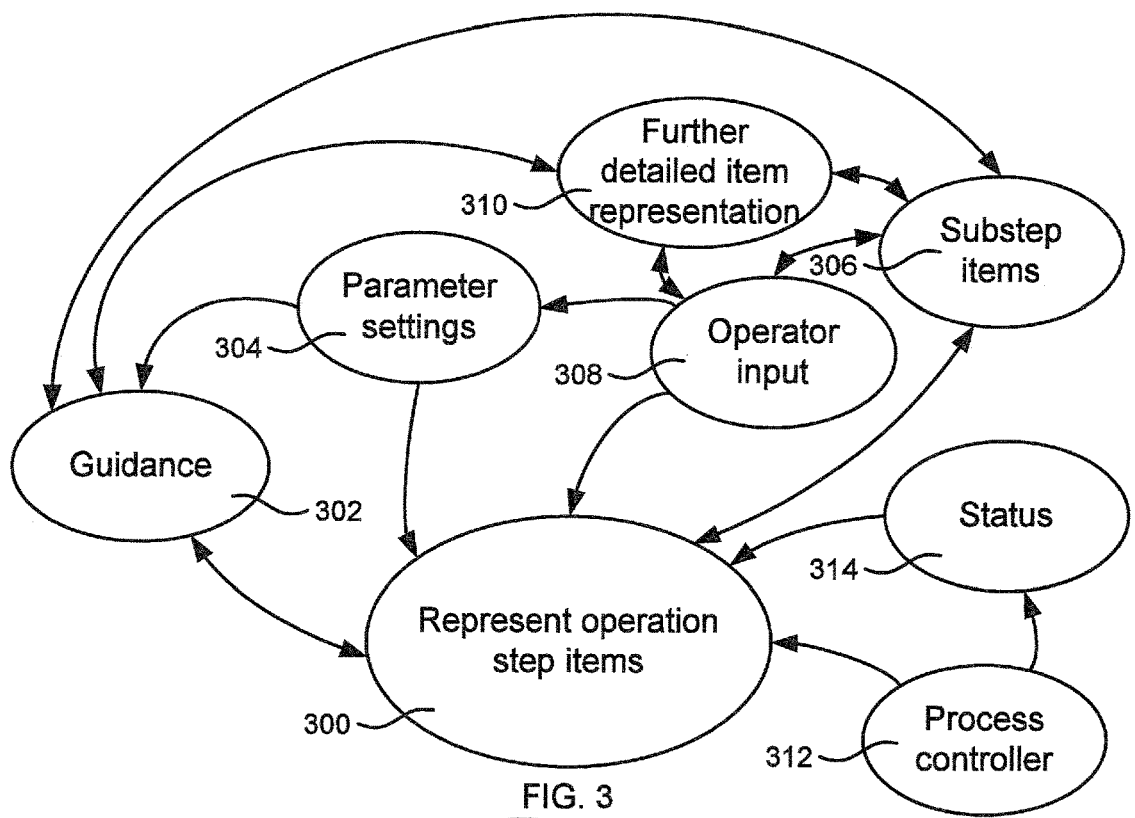
FIG. 3 is an object diagram schematically illustrating assigning representations of operation steps to operation step items suitable for user interface control.

FIG. 3 is an object diagram schematically illustrating assigning representations of operation steps to operation step items suitable for user interface control. The action corresponds to the representing action 202 of FIG. 2.

A representing object 300 is arranged to collect information that may be enabled for user interaction with each operation step and represents that as an operation step item for the respective operation step. The representing object may interact with a guidance object 302 which provides guidance information for the operation step item. The guidance may comprise several levels of detail which may be provided based on information provided from other objects, such as a parameter setting object 304 which may hold a parameter setting indicating the skill and/or training level of the user, e.g. patient, nurse, technician, etc. The level may also be chosen to be more detailed than indicated by such parameters, e.g. upon user request. This may be handled by a substep item object 306 which may call upon a more detailed guidance as a dynamic setting, e.g. upon interaction from an operator input object 308. This substep item object 406 may also interact with an object 310 for further detailed item representation, i.e. some kind of information zoom function. The object 310 may also be a part of the substep item object 306. The object 310 may also interact with the operator input object 308.

The operator input object 308 may interact with the representation object 300, and through this interact with the other objects as well.

Input of the dialysis process and other status may be provided from a process controller object 312 and/or a status tracking object 314 for populating the information of the respective operation step items.

An example of an operation step may be called "Connect concentrates", which includes properly connecting a concentrate unit to the dialysis apparatus, where for example a peripherals/consumables object provides information whether a concentrate unit is connected, wherein a sensor input provided through a sensor input object may be provided either via a peripherals/consumable object of the process controller object 312 or directly to the status object 314. When the concentrate unit is properly connected, this operation step may be determined to be completed based on the information received from the above mentioned objects, but may also require a confirmation from a user via input/parameter settings object for being set as completed. The operation step item may include a basic guidance by the guidance object 302 where the basic guidance includes an indication that the concentrates unit is to be attached and an indication on the type of concentrates unit to use. The substep item object 306 may provide substeps items, e.g. "Open latch X", "Apply unit", "Close latch and confirm action", and the further detailed item object may provide further details on how to apply the unit, e.g. "Turn lever marked A", "Insert unit with text towards you", "Turn back lever marked A". The instructions may be enhanced with images, animations, indicator lights on where to attach unit, etc. The guidance object 302 will be involved in such additional instructions. However, here it should be noted that the representation object does not display anything; it just populates the operation step items with proper information and/or pointers such that it may be used when called upon.

Figure 4:
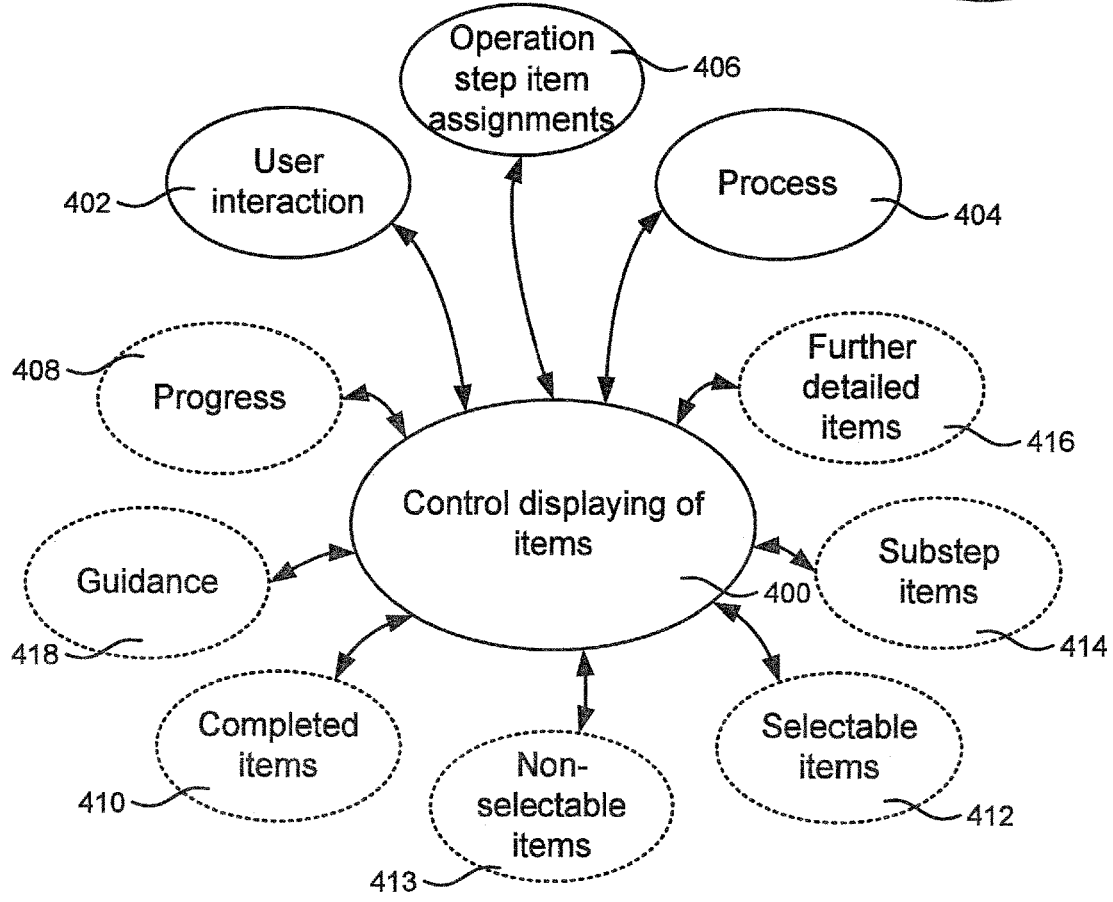
FIG. 4 is an object diagram schematically illustrating the control of display of operation step items through a user interface.

FIG. 4 is an object diagram schematically illustrating controlling of displaying operation step items through the user interface. The action corresponds to the display controlling action 206 of FIG. 2.

A display control object 400 provides control of what is to be displayed through the UI. For providing the desired flexibility for a user to work with the apparatus for dialysis, the control object is arranged to enable two or more of said operation step items assigned a selectable state to be displayed through said UI and enable interaction with those items through the input device. The display control object 400 can gain the knowledge of which operation step items that are selectable and their possible content from the assignment, e.g. structure, object 406, which corresponds to step 204 of FIG. 2. The display control object 400 then selects what information to provide through the UI. This selection may be provided through an information collection from a user interaction object 402 and/or a process object 404, i.e. from man and/or from machine. The display control object 400 may also gain information from a progress object 408 which may determine progress through a series of actions among which some are performed and others are scheduled. This may enhance planning for the operator. The display control object may also get information from a completed items object 410, wherein an operator may be provided information about already completed tasks. An object 412 managing selectable items (and/or a corresponding object 413 managing non-selectable items) provides information to the display control object 400 to enable an informative set-up of displayed items. This together with objects 414, 416 managing substep items and further detailed items, in conjunction with a guidance managing object 418 supports the display control object 400 for providing desired and necessary information through the UI.

Figure 5:
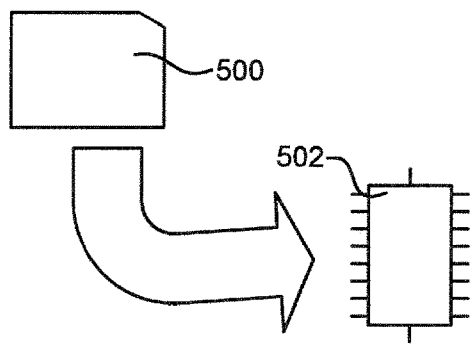
FIG. 5 is an object diagram schematically illustrating assignment of states, preferably forming a structure, preferably data structure, of operation step items.

FIG. 5 schematically illustrates a computer-readable medium for storing a computer program, and a processor for executing instructions of the computer program. The methods according to the present invention are suitable for implementation with aid of processing means, such as computers and/or processors. Therefore, there is provided computer programs, comprising instructions arranged to cause the processing means, processor, or computer of the apparatus for dialysis, e.g. its process controller and/or UI controller to perform the steps of any of the methods according to any of the embodiments described with reference to FIGS. 2 to 4. The computer programs preferably comprises program code which is stored on a computer readable medium 500, as illustrated in FIG. 5, which may be loaded and executed by a processing means, processor, or computer 502 to cause it to perform the methods, respectively, according to embodiments of the present invention, preferably as any of the embodiments described with reference to FIGS. 2 to 4. The computer 502 and computer program product 500 may be arranged to execute the program code sequentially where actions of any of the methods are performed stepwise. The processing means, processor, or computer 502 is preferably what normally is referred to as an embedded system. Thus, the depicted computer readable medium 500 and computer 502 in FIG. 5 should be construed to be for illustrative purposes only to provide understanding of the principle, and not to be construed as any direct illustration of the elements.

Figure 6:
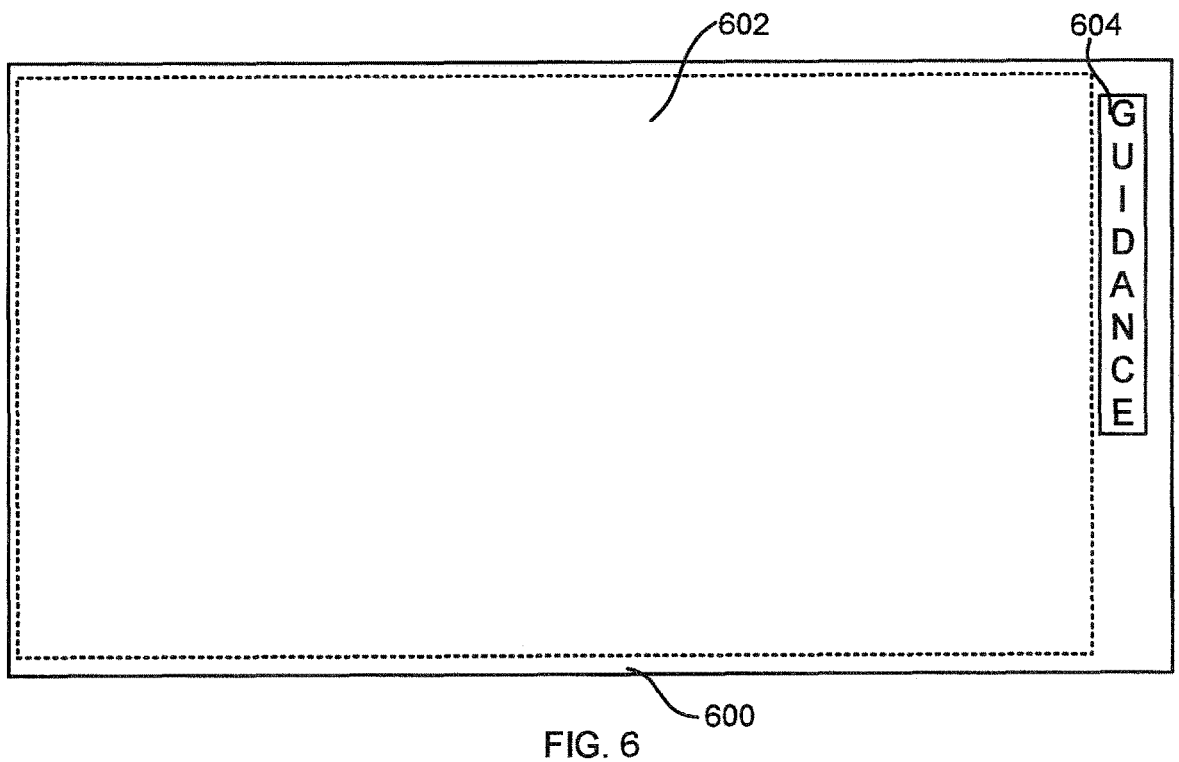
FIG. 6 is an object diagram schematically illustrating controlling of displaying operation step items through the user interface.

FIG. 6 illustrates a principle for a UI screen 600 with one or more operation step items 602 and a button 604 on the UI by which the operator is enabled to press the button 604 until the desired amount of information and guidance is displayed.

Figure 7:
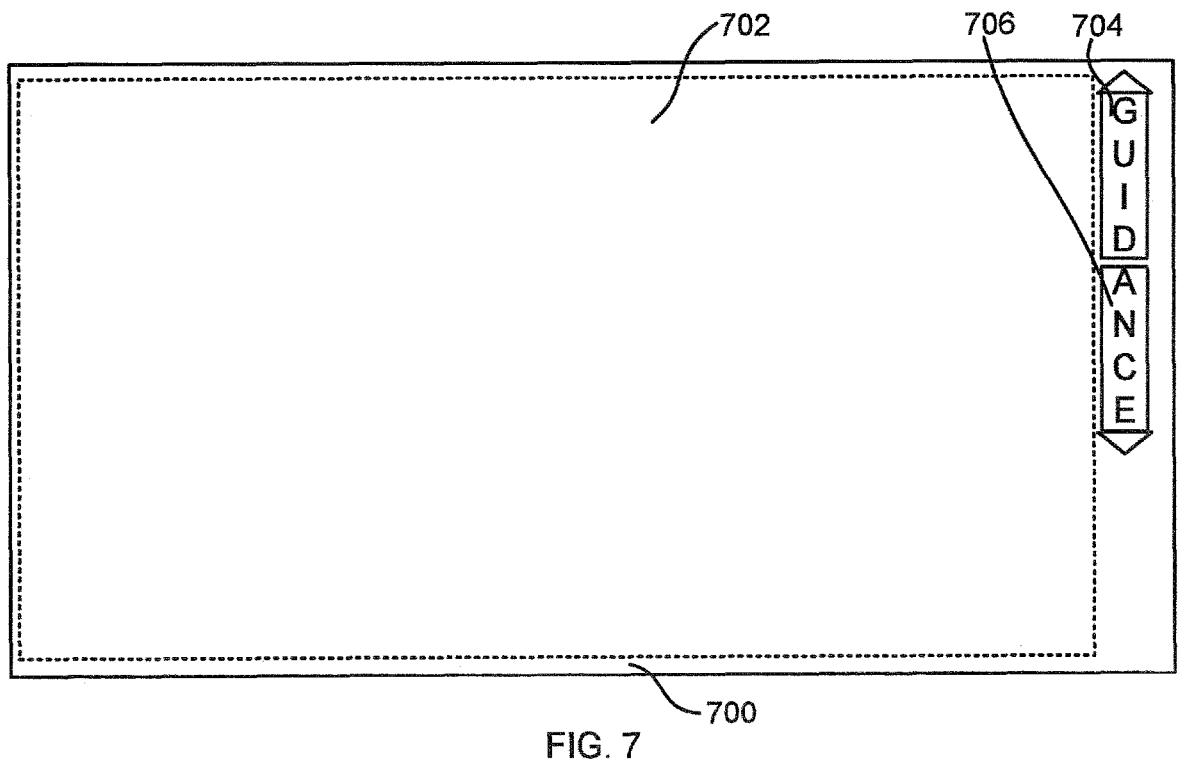
FIG. 7 schematically illustrates a computer-readable medium for storing a computer program, and a processor for executing instructions of the computer program.

FIG. 7 illustrates another principle for a UI screen 700 with one or more operation step items 702 and a button set 704, 706 on the UI where the operator is enabled to press "MORE" button 704 or "LESS" 706 button for changing the amount of guidance. In this example, a button 704, 706 may be marked, e.g. greyed-out, when there are no further levels of "MORE" or "LESS" guidance to be provided by the UI.

FIGS. 8 to 25 illustrate examples of displayed information according to various embodiments. The illustrations may also be considered as two examples provided according to an embodiment where different settings for the amount of information to be provided are applied to the one and same UI. Thus, FIGS. 8 to 21 illustrate a user interface example according to a first user interface setting providing more guidance and FIGS. 22 to 25 illustrate a user interface example according to a second user interface setting providing less guidance, which may be set by the user during operation as discussed above. An example of a button 850, similar to the example of FIG. 6, for this is illustrated in FIGS. 8 to 17 and 19 to 25, but other examples, e.g. the one illustrated in FIG. 7, are equally combinable with the examples illustrated in FIGS. 8 to 25. The first user interface setting may be considered suitable for less trained operators since it provides detailed guidance, while the second user interface setting may be considered suitable for more trained operators and provides less interaction with the user interface which may make work more efficient for the more trained operator.

Figure 8:
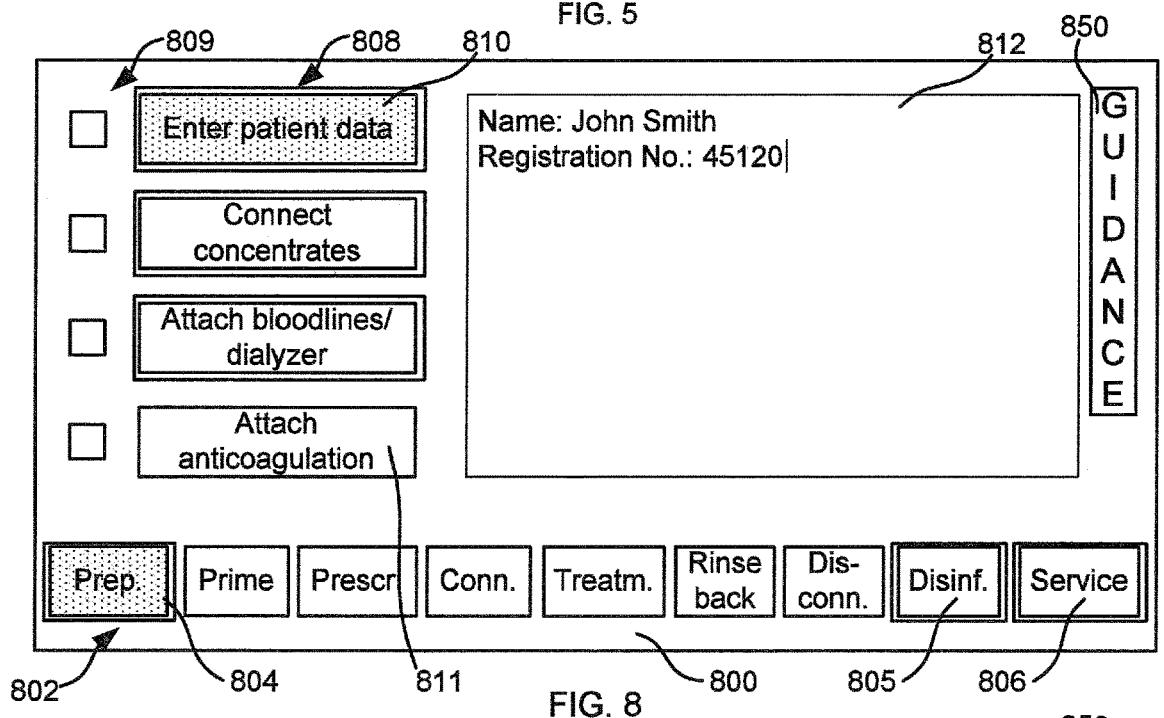

FIG. 8 illustrates a snap shot of a display screen 800 of a UI according to an embodiment. The UI in this example has a touch screen, i.e. the visual output device and the input device are integrated and aligned such that interaction may be made directly on the displayed items for such items that are assigned for interaction. In the display, a number of operation step items 802 are displayed, among which some operation step items 804, 805, 806 are selectable which is indicated in some way, e.g. by an additional frame or shadowing around the respective item. Colour schemes may also be used for the indication.

In the snap shot of the display screen 800, a user has interacted with operation step item 804, which is then indicated as active, i.e. that interaction on the operation step item is ongoing, by for example the displayed operation step item 804 being dotted (also here, a colour scheme may be used). The interaction has called upon displaying of a number of subitems 808 which are displayed, and corresponding check boxes and/or status indicators 809 may also be displayed. Such check box and/or status indicators may also be provided for any of the operation step items 802. As an alternative, or additionally, an indication in the operation step item may be provided, as will be illustrated with reference to FIG. 11 where a completed item is illustrated with hatching. Other patterns and/or colour schemes may also be used for the illustration.

In the snap shot of the display screen 800, a user has interacted with operation substep item 810, which then is indicated as active, i.e. that interaction on the operation step item is ongoing, by for example the displayed operation step item 804 being dotted (also here, a colour scheme may be used). The interaction has called upon entering information associated with the operation substep item 810 which is enabled to be entered in a work area 812 of the display screen 800. This guided interaction field area 812 may be used for such input, e.g. with aid of a keyboard, keypad or the like, but may also be used for guidance information, displaying of settings or parameters, sensor values, progress information, etc. A corresponding indicator 809 may indicate completion upon the completed input. A signal on the completed input may be generated upon the operator actuating an enter/OK (soft) button.

In the snap shot of the display screen 800 it may also be seen that operation substep item 811 is not indicated as active. This is an indication to the user that this operation substep item 811 is not ready for being performed, and the processor has determined this operation substep item 811 as being available only after completion of another operation step or operation substep.

Figure 9:
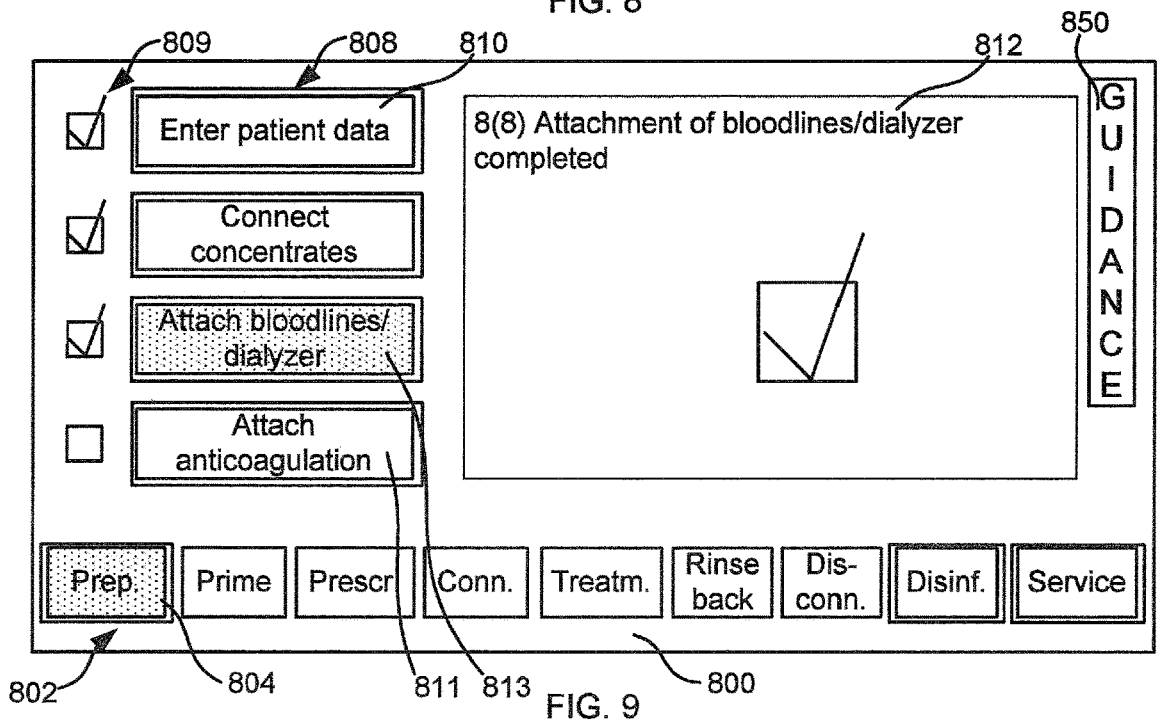

FIG. 9 illustrates a snap shot of the display screen 800 of the UI at a later time instant than that for FIG. 8, and here some of the operation substeps of items 808 are completed, which is indicated by the indicators 809. Operation substep item 813 is indicated as selected, and the guided interaction field 812 displays an operation substep item on a further level of detail related to the operation substep item 813. The operation substep on the further level of detail is illustrated to be 8 of 8 and indicates that attachment of bloodlines and/or dialyzer is completed. Thus, the former non-illustrated seven substeps on the further level of detail preferably have guided the user, step-by-step, to make the attachment. This allows for the less trained user to make the attachment correct (or for the trained user to feel more safe). As discussed above, the trained user who knows the attachment steps well, the substeps on the further level of detail need not be displayed, and the trained user may just go on with the actions. This will be further discussed with reference to FIGS. 21 to 25. Here, the operation substep item 811 has become selectable, and is indicated as selectable with a frame. The processor has been able to determine this selectable condition since operation substeps on which the operation substep of operation substep item 811 depends have been completed.

Figure 10:
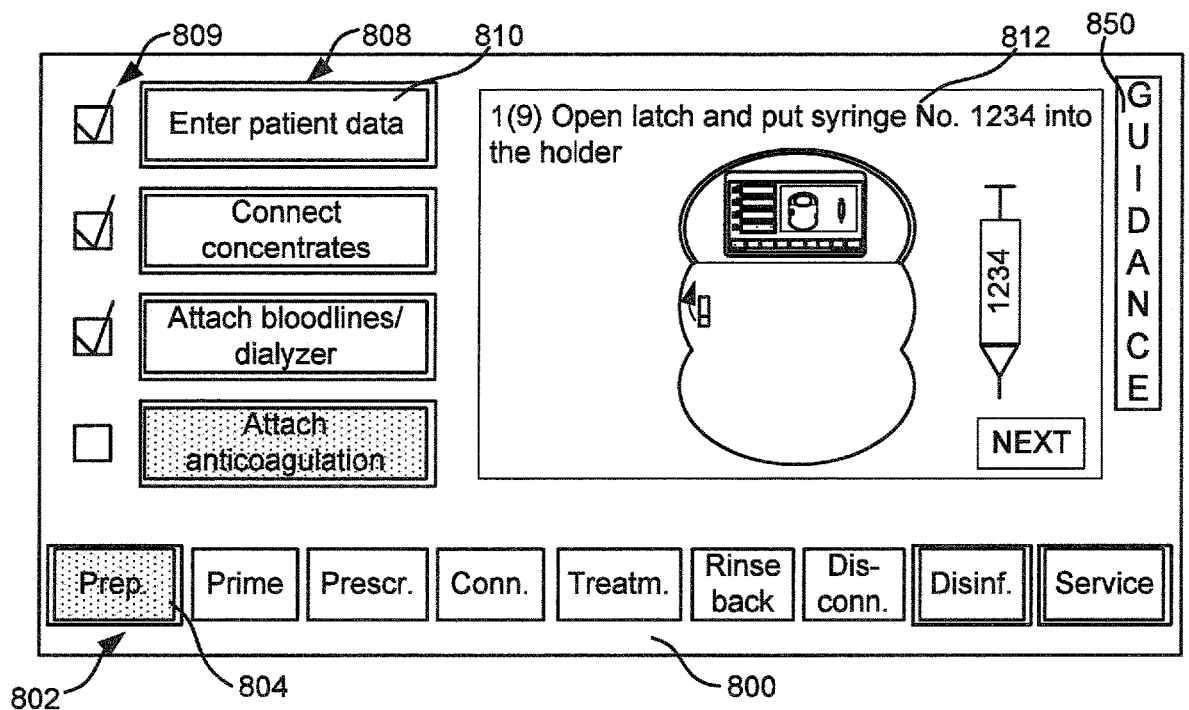
Figure 11:
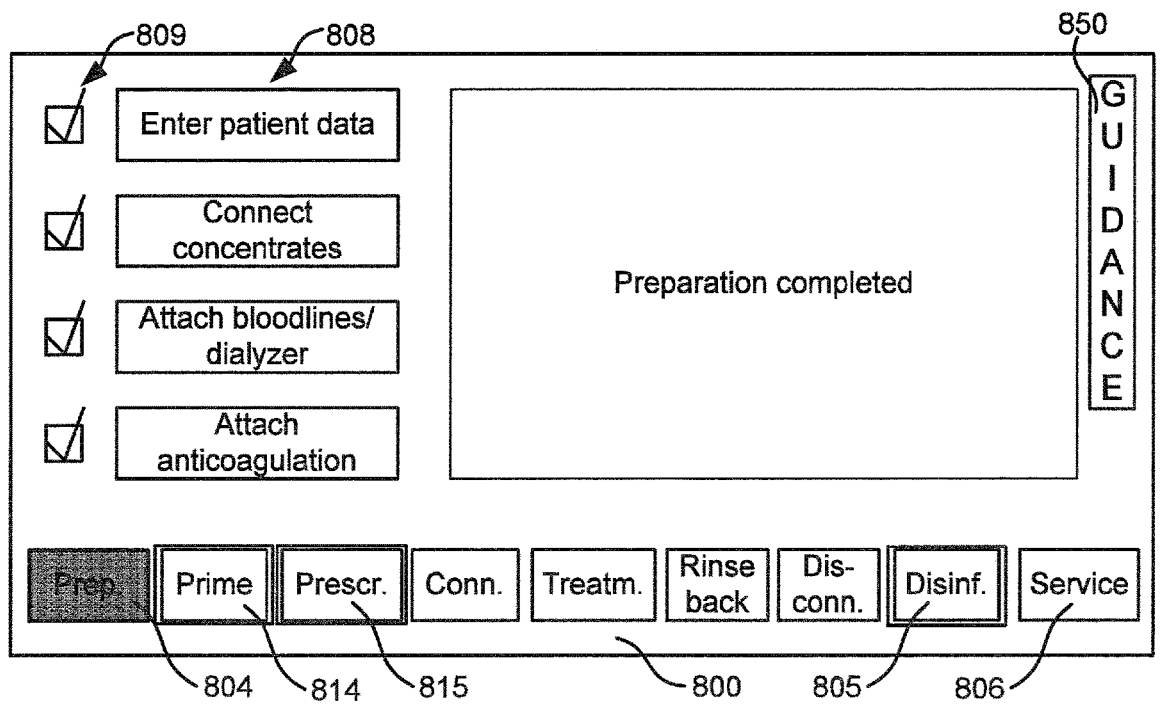

FIG. 10 is a further snap shot where the user has selected operation substep 811, and a first of nine operation substep items on a further level of detail related to the operation substep item 811 is displayed in the guided interaction field 812. Here, guidance is provided to the user. The user may press the "NEXT" soft key to proceed to the next operation substep item on a further level of detail, and/or the processor may jump to the next operation substep item on a further level of detail when sensors of the apparatus indicates that the illustrated action has been performed. FIG. 11 illustrates a snap shot of the display screen 800 of the UI at a later time instant than that for FIGS. 8 to 10, and here all the operation substeps of items 808 are completed, which is indicated by the indicators 809. Since these operation substeps are completed, and thereby operation step of item 804 is completed, the operation step item 804 is indicated as completed with the hatching. Further, operation steps of items 814 and 815, which are sequential of operation step of item 804, are now selectable which is indicated on the display screen 800 accordingly. Still further, the operation step item 806 is now no longer selectable since this operation step may interfere with the function of the apparatus in the current state.

In the above illustrations, for the sake of easier understanding, several non-selectable operation step items are displayed. However, e.g. for the sake of screen area economy or easier overview, the displaying of such operation step items may be omitted. For example in FIG. 11 when the "Service" operation item 806 is no longer selectable, the displaying of this item may be omitted to leave room for the other operation step items or for any other item, such as an indicator, progress bar, information item, etc.

In FIG. 11, the operator may select if the "Prime" operation step 814 or the "Prescription" operation step 815 should be performed next since there is no dependency between these operation steps. The "Disinfection" operation step 805 is also selectable since it does not interfere with the present state of the dialysis procedure. In the description below, it is assumed that the user selects the priming operation step before the prescription operation step such that the priming may proceed while the prescription step is taken care of. However, the opposite order is equally possible in this example. Further, for the sake of time saving, the priming operation step 814 may here be indicated as recommended next operation step, although any of the priming operation step 814 and the prescription operation step 815 are selectable.

Figure 12:
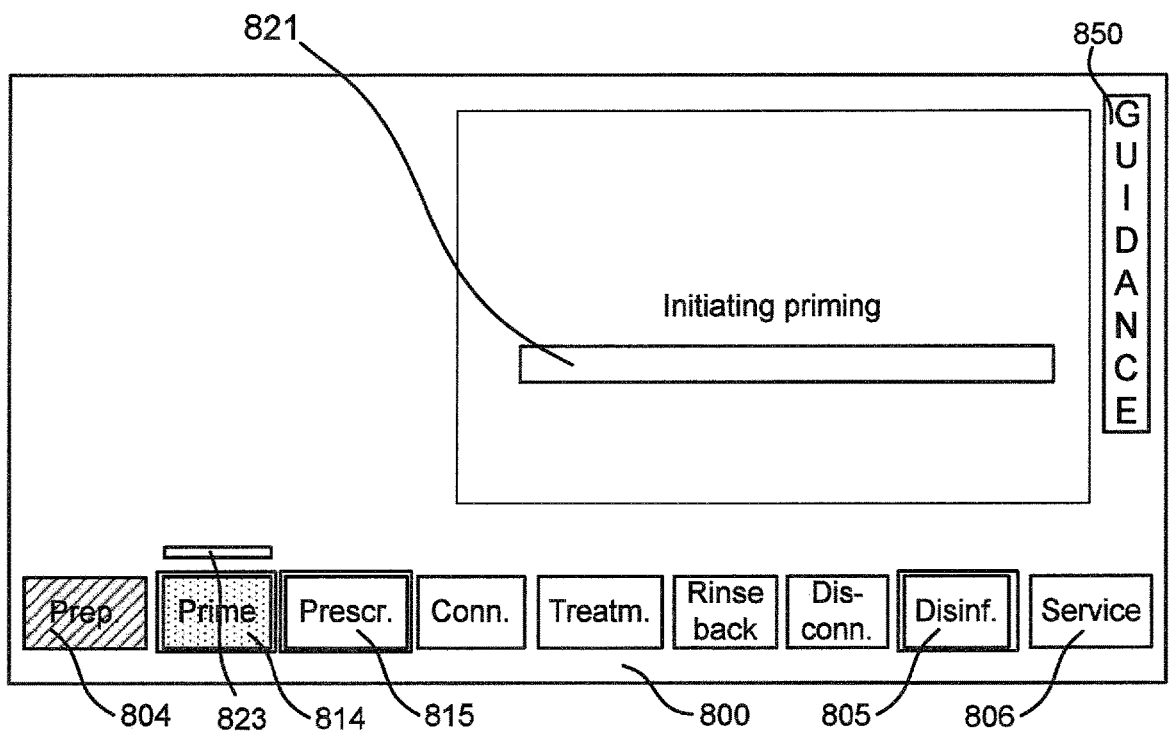
Figure 13:
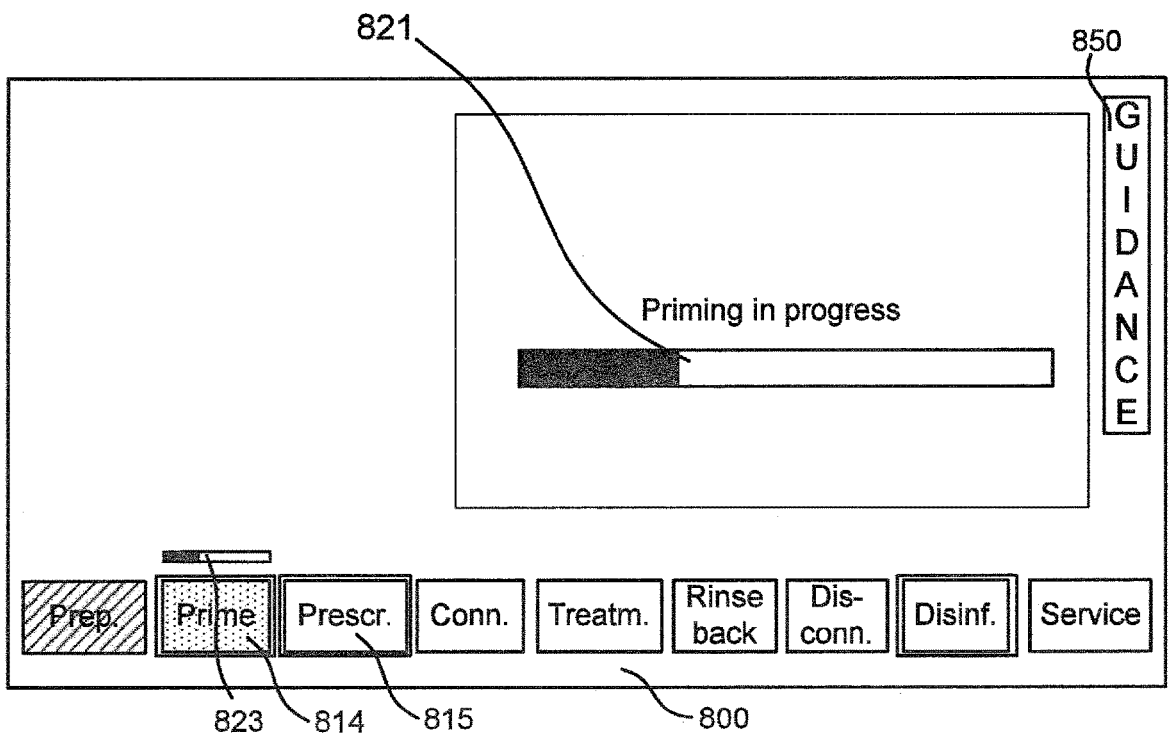

FIG. 12 illustrates a snap shot of the display screen 800 of the UI at a later time instant than that for FIG. 11, where operation step item 814 is interacted with and information is provided that priming is initiated. Here it may be noted that operation step item 806 is not selectable for similar reasons as demonstrated above, while the same operation steps that were available in FIG. 11 are still available. FIG. 13 illustrates a corresponding screen at a later instant where a progress bar 821 may be displayed indicating the progress of priming. A miniature 823 of the progress bar 821 may also be provided in connection with the operation step item 814.

Figure 14:
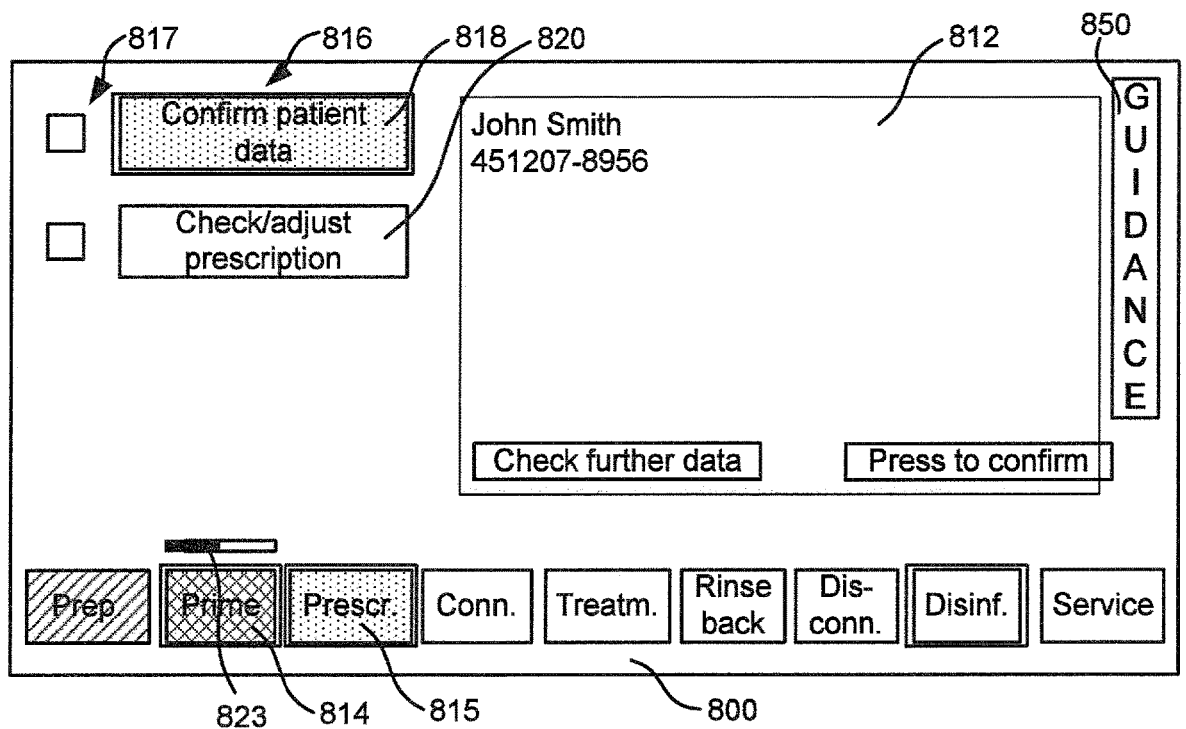

FIG. 14 illustrates a snap shot of the display screen 800 of the UI at a later time instant than that for FIG. 13, where operation step item 815 is interacted with, and a number of operation substep items 816 are displayed, also here with optional check box or status indicators 817. Operation substep item 818 is activated, by the operator through interaction or by the UI controller as a suggested next action, and corresponding information and/or input prompts are displayed in the guided interaction field area 812. It should be noted that operation step item 814 may be indicated as being in progress, here indicated with a fishnet area of the operation step item 814. Further, a progress bar may be provided in connection with the operation step item 814.

Figure 15:
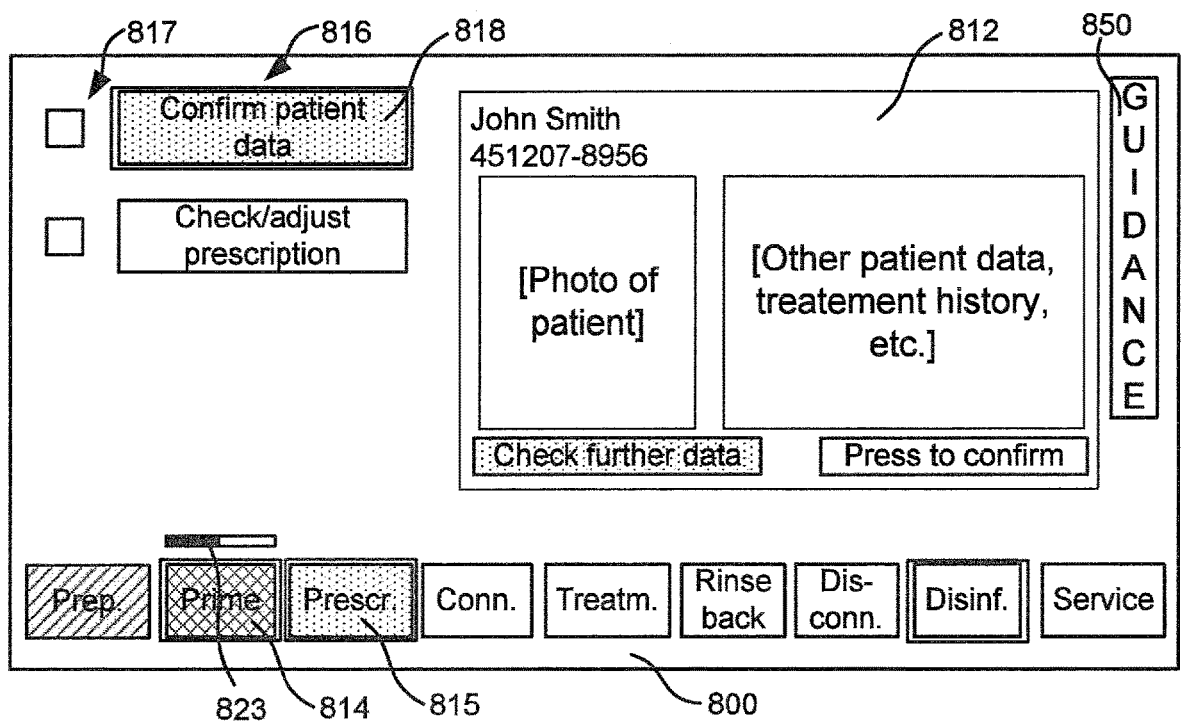
Figure 19:
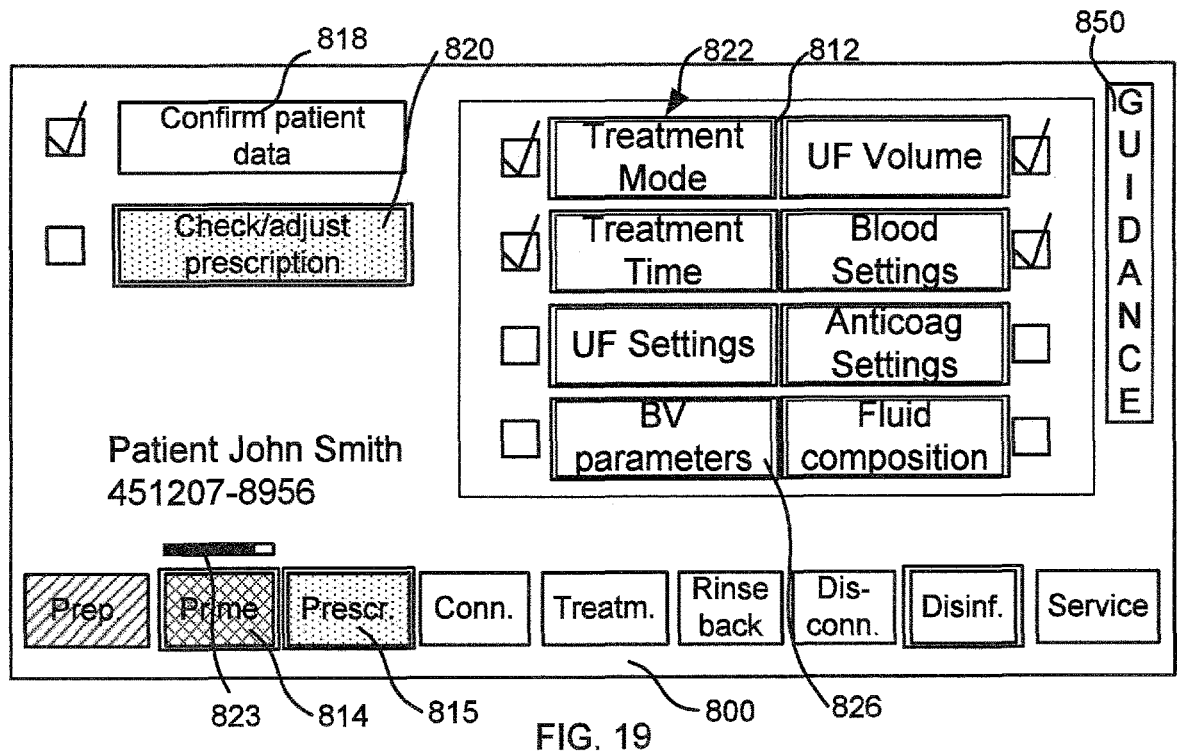

Here, operation substep item 820 is not selectable since it is depending on completion of or depending on confirmation of patient data operation substep item 818. The patient data may be presented in the guided interaction field 812, and optionally may soft buttons be provided for checking details and/or confirming be provided in the guided interaction field 812. FIG. 15 illustrates that the user has pressed the "Check further data" button in the guided interaction field, wherein further information about the patient is presented in the guided interaction field, and the user may confirm if the patient data is correct. Upon such confirmation, as illustrated in FIG. 16 which illustrates a snap shot of the display screen 800 of the UI at a later time instant than that for FIG. 15, the operation substep of item 818 is indicated as completed and operation substep item 820 may be activated. FIG. 17 illustrates that operation substep item 820 is selected. Similar to what is demonstrated for substep item 818, the selection may be activated by the operator through interaction or by the UI controller as a suggested next action. A number of items 822 of further detail corresponding to operation substep of item 820 are displayed, e.g. in the guided interaction field area 812. Here, in the snap shot of the display screen 800 of the UI, some of the items of further detail are completed which is indicated. At least some of the items 822 of further detail may be activated to for example view a parameter setting view, as illustrated in FIG. 18 which corresponds to activation of the item 824 of further detail, e.g. in the guided interaction field area 812. Other views may be guidance, such as text, images and/or animations, which may be viewed upon interaction of an item of further detail. Further, operation substep of further detail 826 related to blood volume (BV) parameters is indicated as non-selectable since this requires that a blood volume sensor (BVS) is installed. Upon any interaction by the operator with the non-selectable item 826, the UI may provide an instruction view telling the operator that this substep is only available upon installation of the BVS, and optionally/selectably may also information about installation be provided. Sensors of the apparatus monitors whether a BVS is installed, and upon sensor input that the BVS is installed, BV parameters may be set, as illustrated in FIG. 19. Corresponding sensor dependencies may be present for other operation steps, operation substeps, etc.

Figure 20:
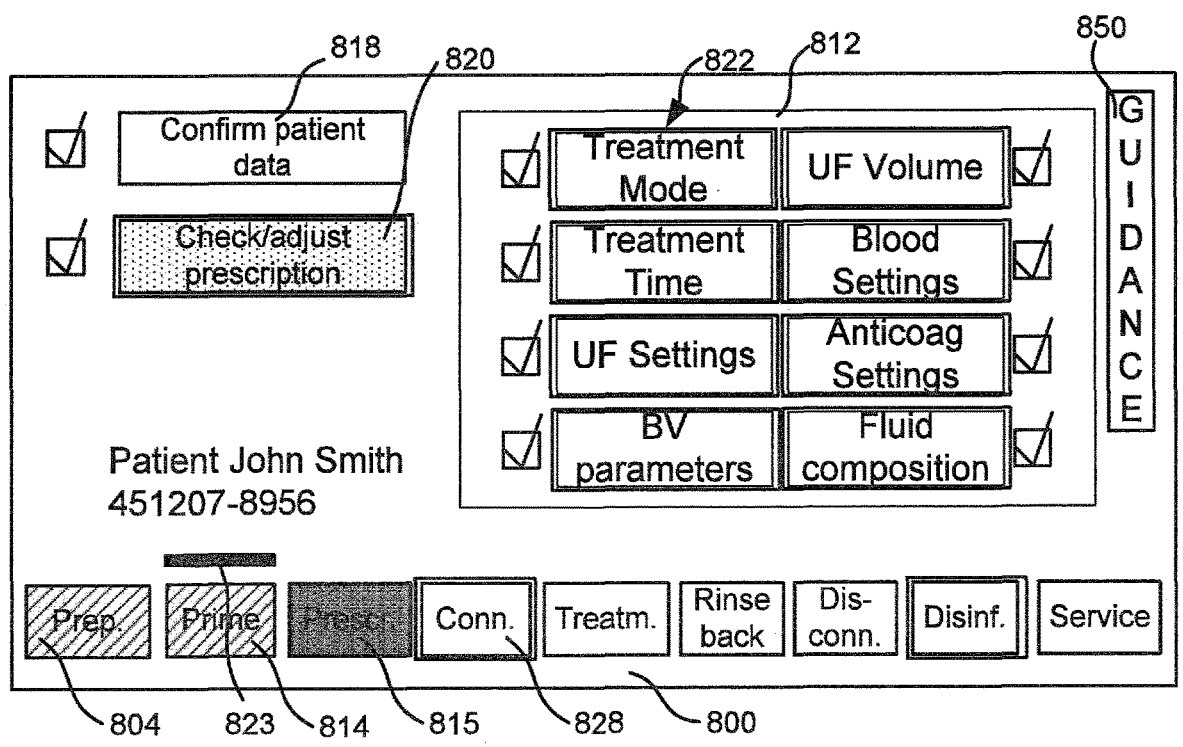
Figure 21:
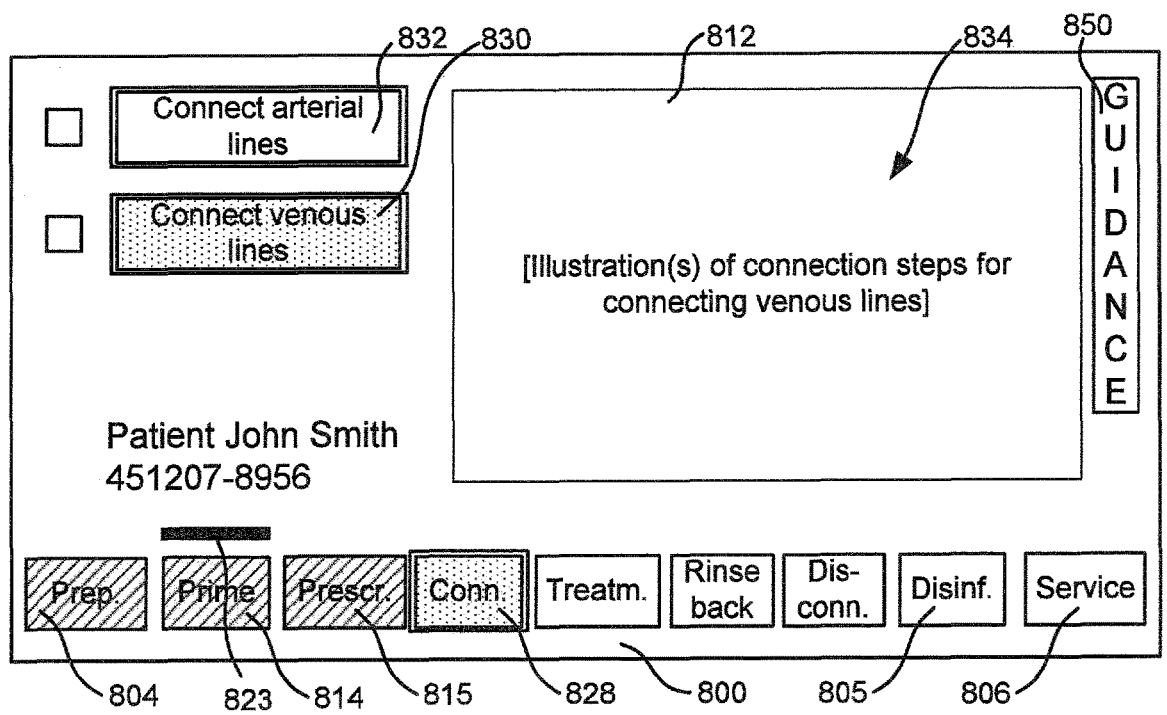

FIG. 20 illustrates a snap shot of the display screen 800 of the UI at a later time instant than that for FIG. 19, where the operation substeps of items 818 and 820 are completed and operation step item 828 becomes selectable. Upon selection of operation step item 828, as illustrated in FIG. 21, guidance and/or substeps, etc., are provided corresponding to the principles that have been demonstrated above. In FIG. 21, both operation substep items 830 and 832 are selectable, and the user has here selected operation substep item 830, wherein illustrative guidance 834 is provided in the guided interaction field 812. Here it may be noted that operation step item 805 is not selectable for similar reasons as demonstrated above. The operation step items 804, 814 and 815 indicate their corresponding operation steps as completed. Here, all the completed operation step items are displayed, but that is not necessary. For the same reasons as demonstrated above for non-selectable operation step items, the displaying of one or more of the completed operation step items may be omitted due to screen area economy and/or overview considerations. It is also preferable that completed operation step items may be interacted with, although not selected, to enable view of performed actions, states or settings. This may for example be of interest when shifting user during the process, e.g. from night shift to day shift. This may be provided as a particular guidance state therefor or be provided in a detailed guidance state called upon by the user during operation, e.g. as demonstrated with reference to FIGS. 6 and 7.

By the approach demonstrated by the example screen snap shots of FIGS. 8 to 21, a very detailed guidance through the process for dialysis may be provided. This detailed guidance may be mandatory for some users, as discussed above, for safeguarding the proper handling through the process. It may also be optional and selectable during operation as discussed above. One example is that the most detailed guidance is mandatory for a user that is not particularly trained for the particular process, e.g. a patient performing home dialysis, or a nurse at a trauma centre (being very skilled in other medical issues, but less in dialysis procedures). There may be different levels of guidance, as can be understood from the demonstration above of operation steps, operation substeps, operation steps of further detail and setting and guidance on a still further level of detail. A particularly trained user, such as a nurse at a dialysis centre, may for example only have the operation steps as mandatory, i.e. the state with least guidance, on which an example will be given with reference to FIGS. 22 to 25. However, for such a particularly trained user, the option to get further guidance, as of e.g. FIGS. 8 to 21, can also be beneficial in some situations, e.g. after returning from a long vacation. It is to be noted that the restrictions on different guidance states are only optional.

Figure 22:
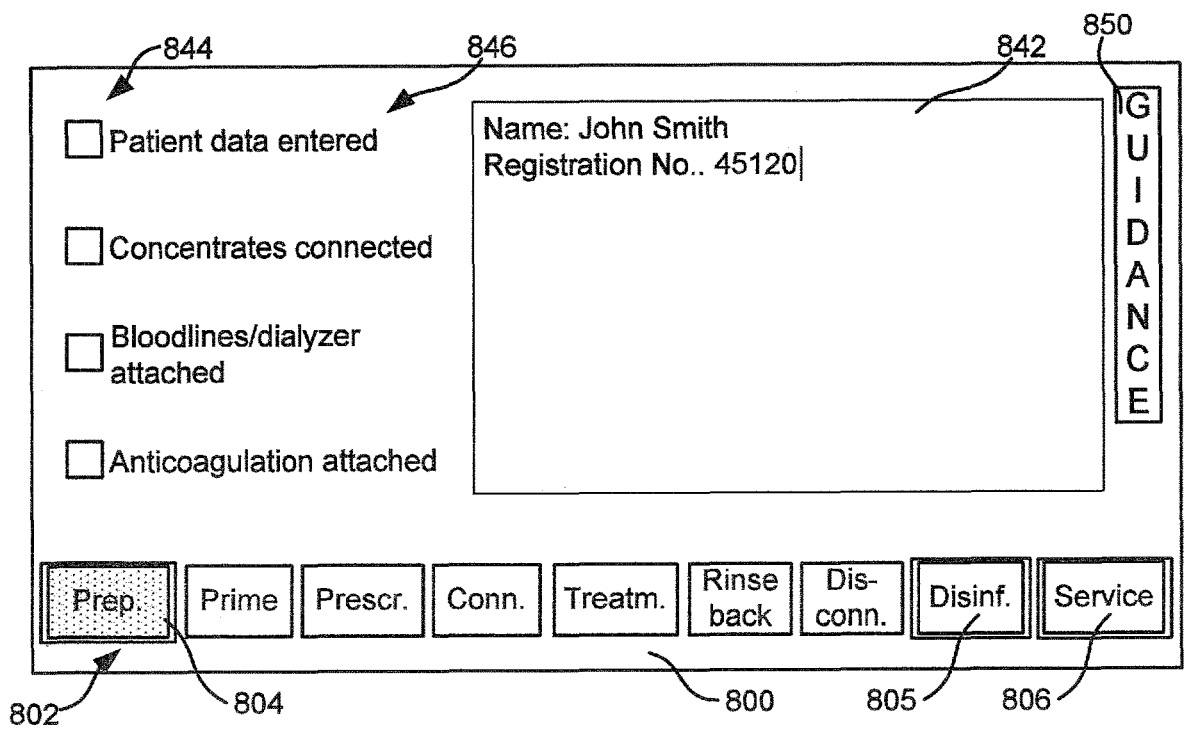
FIGS. 22 to 25 illustrate a user interface example according to a second user interface setting.

FIG. 22 illustrates a snap shot of a display screen 800 of a UI according to an embodiment. The type of touch display and way of indicating operation step items 802 is similar to what is demonstrated with reference to FIGS. 8 to 21 for easier comparison of the approaches, and the work area that in the examples demonstrated with reference to FIGS. 8 to 21 was a guided interaction field is here an input field 842. Here, a check field with check boxes 844 and issue descriptors 846 may be provided for the respective operation step items 802 upon selection. The check boxes 844 are checked by the user and/or when sensor signals indicates that the respective issue is solved/performed. Thus, the trained user may perform the steps with minimized interaction with the user interface. In FIG. 22, the preparation operation step item 804 is selected, wherein the issue descriptors 846 and their check boxes are displayed. The input field 842 displays a form for manual entry of patient data. The user may thus type the patient data, but if for example an electronic patient card or patient data server is read, the patient data is automatically entered and the check box for entering patient data becomes ticked. The other check boxes are preferably ticked based on sensor signals of sensors monitoring connections and attachments. The user may also tick the boxes manually upon performed actions.

For the easier understanding, the operation steps, substeps, substeps of further detail and items of still further detail, etc. has been explained as if all being mandatory, but that is not necessarily the case. As is understood from the disclosure above, the service operation step is not mandatory for the dialysis, but this may also apply for some substeps, substeps of further detail and items of still further detail, etc. In some embodiments, such exclusively optional operation steps, substeps, substeps of further detail and items of still further detail, etc. may be indicated as such by the corresponding displayed items.

Figure 23:
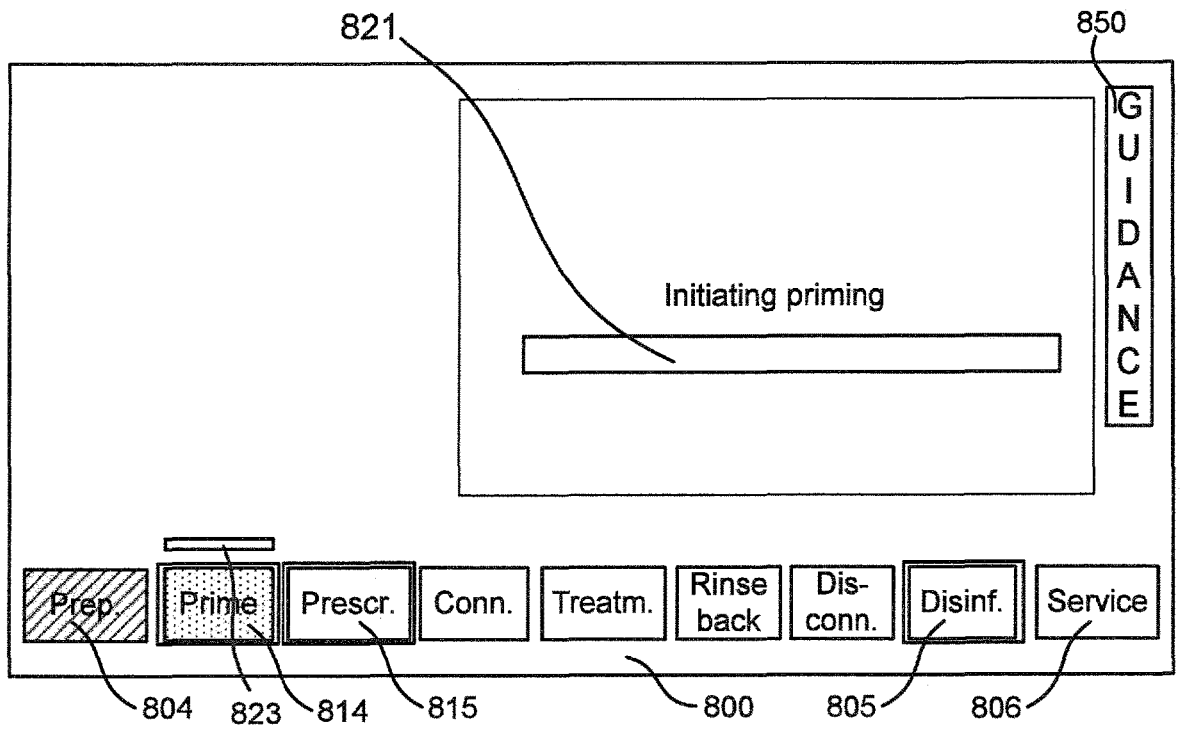

FIG. 23 illustrates a snap shot of the display screen 800 of the UI at a later time instant than that for FIG. 22, where the operation step of item 804 is completed and operation items 814 and 815 become selectable. The user has here selected the priming operation step item 814 and the priming is initiating. Consequently, the service operation step item 806, as demonstrated above, is no longer selectable.

Figure 24:
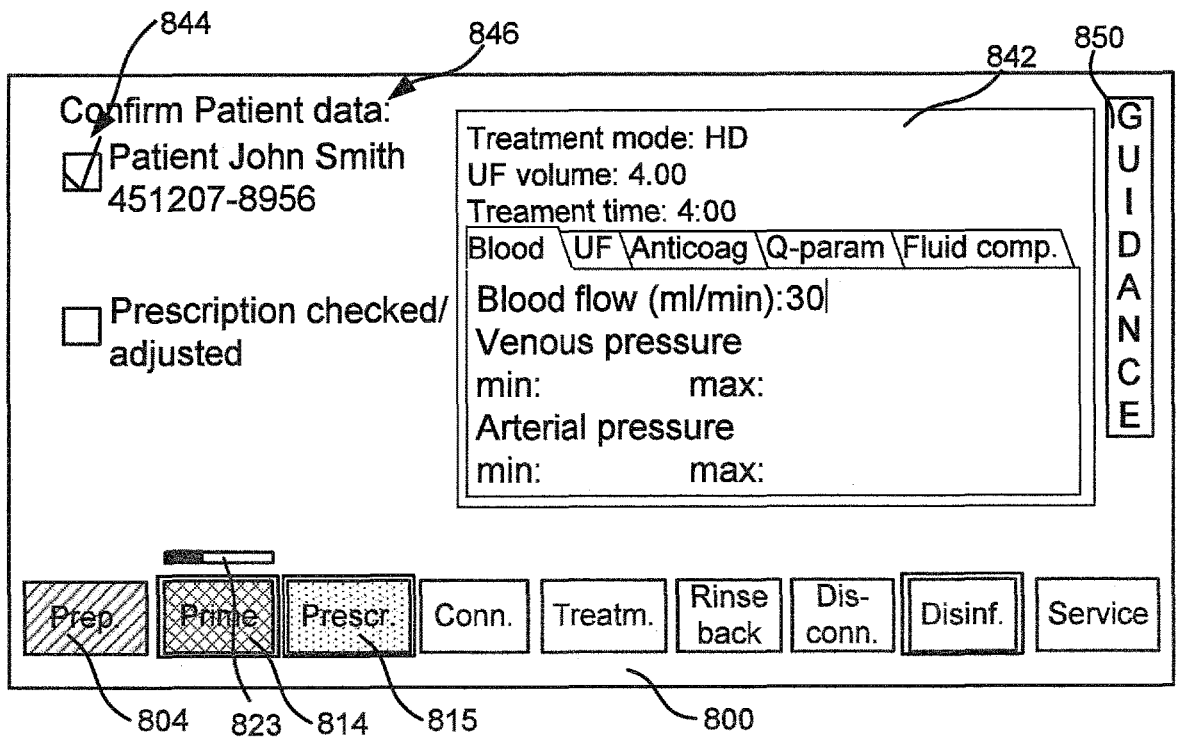

FIG. 24 illustrates a snap shot of the display screen 800 of the UI at a later time instant than that for FIG. 23, where the operation step of item 804 is indicated as completed and operation item 814 is indicated as in progress. The user has here selected operation step item 815, and an input form for prescription parameters is displayed in the input field 842. Check boxes and issue descriptors are also displayed and the user may tick the check boxes to confirm patient data, as performed in FIG. 24, and the prescription parameters.

Figure 25:
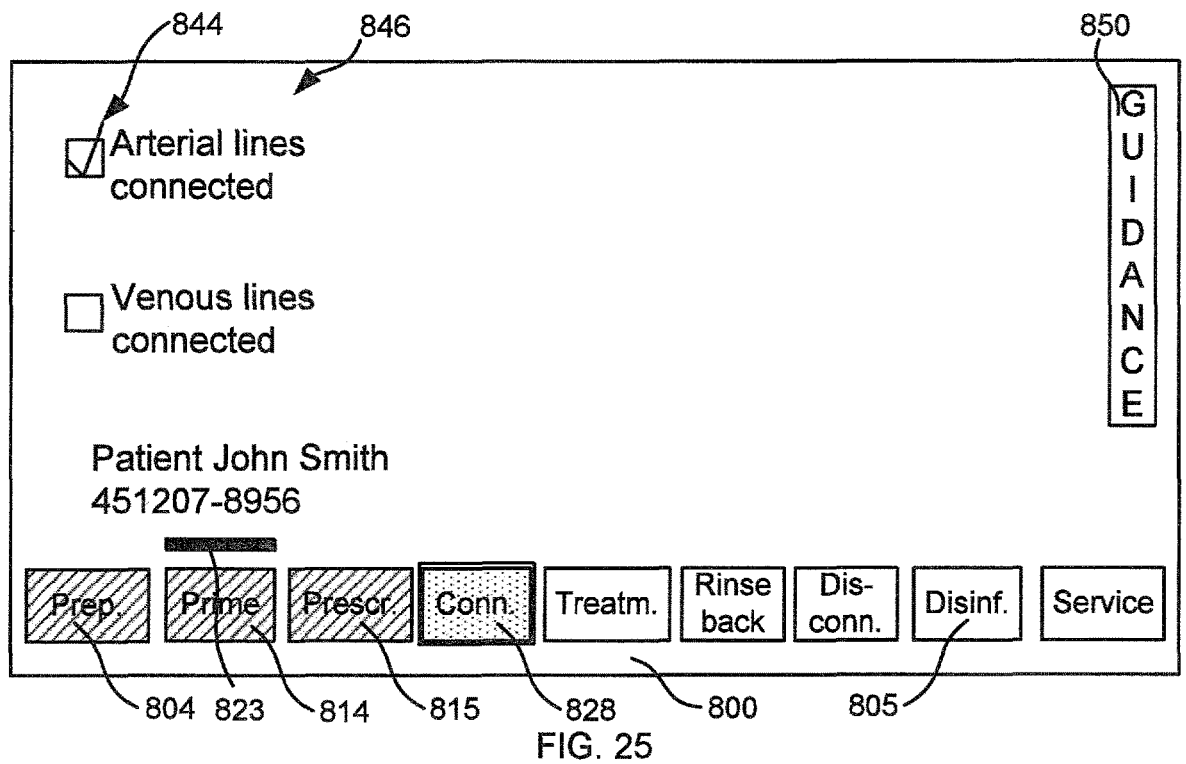

FIG. 25 illustrates a snap shot of the display screen 800 of the UI at a later time instant than that for FIG. 24, where the operation steps of items 804, 814 and 815 are completed and operation step item 828 is selected. The user ticks off the check boxes as the actions are performed, and the procedure continues according to the here demonstrated principles. Here it can be noted that operation step item 806 is not selectable for similar reasons as demonstrated above.

The examples given with reference to FIGS. 8 to 25 give an illustrative view on how the principles may be applied for examples of dialysis processes and dialysis apparatuses. The reader skilled in the field of technology readily understands that the operation steps of the examples may be others than those mentioned, and the operation step items may look different from those depicted.

As can be readily recognised when comparing the approach demonstrated with reference to FIGS. 8 to 21 and the approach demonstrated with reference 22 to 25, the approach of FIGS. 22 to 25 requires that the user knows the actions to be made, but the process can be progressed with much less interaction with the UI. The particularly trained user can thus make progress in the process in a way that may be experienced smother and faster. If the particularly trained user anyway wants to get more guidance or use any of the input screens as of any of FIGS. 8 to 22, that may be called upon through the user interface. The versatility for the particularly trained user is thus enhanced. The levels of detail, e.g. presentation of operation step items, operation substep items, items of further detail and items of still further detail, etc. may thus be considered as an information zoom tool where more or less detailed guidance and/or guided input screens may be provided.

Since the amount of guidance may be changed during the process, the operator is able to get some screens with a lot of guidance and then to choose to switch to have screens with less guidance, or the other way around. For example, an operator has progressed through screens as illustrated in FIGS. 22 to 24 but when coming to the connection step desires to have more guidance. The operator then presses the "GUIDANCE" button 850, and a screen as of FIG. 21 appears instead of a screen as of FIG. 25. Similar, an operator who has progressed through screens as illustrated in FIGS. 8 to 11 may desire less guidance thereafter and presses the button 850 and then proceeds with a screen as illustrated in FIG. 23. Similar applies for an implementation with states for more than two levels of guidance.

The invention has mainly been described above with reference to a few embodiments. However, as is readily appreciated by a person skilled in the art, other embodiments than the ones disclosed above are equally possible within the scope of the invention, as defined by the appended patent claims.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An apparatus for performing a plurality of operation steps of a dialysis process, said apparatus comprising:
   a process controller for controlling the apparatus to perform the operation steps of the dialysis process, monitor process progress of the dialysis process and monitor sensor inputs from sensors of the apparatus; and
   a user interface ("UI") comprising a display, an input device and a UI controller, wherein the UI controller is configured to enable presentation of graphical data on the display, and wherein the UI controller is configured to enable user interaction with the graphical data and is configured to exchange information with the process controller, wherein the exchanged information is based on the user interaction via the user interface and the process progress of the dialysis process and sensor inputs from the sensors monitored by the process controller, wherein
   the UI controller is configured to represent each of the operation steps by one or more operation step items, each of which is a graphical item suitable to be presented on said display and is selectable by an operator if its corresponding operation step is available, and wherein an amount of operation guidance information of an operation step item is selectable by the operator during the dialysis process to be in one guidance state among a set of guidance states comprising at least a first and a second guidance state, wherein the second guidance state provides a larger amount of guidance than the first guidance state by assigning additional operation guidance information of one or more operation step item selectable for multiple operation steps of the dialysis process, wherein the UI controller maintains the second guidance state over multiple operation steps of the dialysis process while the second guidance state is selected, and wherein the operator is enabled to toggle between the guidance states during the dialysis process, wherein at least one of the operation step items includes operation substep items that represent substeps of the at least one operation step by at least one of operation guidance, parameter setting and status information, wherein the UI controller is arranged to enable display of the operation substep items upon display of the corresponding operation step item when in another guidance state than the first guidance state, and wherein the UI controller is arranged to enable display of a subset of the operation substep items upon display of the corresponding operation step item associated with the subset of operation substep items based on an input from the operator when in the second guidance state, wherein such enabling based on input from the operator overrides any corresponding disabling of the display of the operation substep items by the UI controller when in the first guidance state.

2. The apparatus according to claim 1, wherein one or more operation step items of said operation step items are recommended by the UI controller to be performed next, and are presented with an indicator representing the recommendation, when in a guidance state other than the first guidance state.

3. The apparatus according to claim 1, wherein the UI controller is arranged to disable selection of the first guidance state based on a determined skill level of the operator to be lower than a threshold.

4. The apparatus according to claim 1, wherein the UI controller is arranged to disable display of a subset of the operation substep items upon display of the corresponding operation step item associated with the subset of operation substep items based on an input from the operator when in another guidance state than the first guidance state.

5. The apparatus according to claim 1, wherein the set of guidance states comprises a third guidance state, wherein the third guidance state provides a larger amount of guidance than the second guidance state over multiple operation steps of the dialysis process, and at least one of the operation substep items comprises operation substep items on a further level of detail that represent operation substeps on a further level of detail of the at least one substep by at least one of operation guidance, parameter setting and status information, and wherein the UI controller is arranged to enable display of the operation substep items on a further level of detail upon display of the corresponding operation substep item when in the third guidance state.

6. The apparatus according to claim 5, wherein the UI controller is arranged to enable the display of the operation substep items on a further level of detail upon display of the corresponding operation substep item based on an input from the operator, wherein such enabling based on input from the operator overrides any corresponding disabling of the display of the operation substep items on a further level of detail by the UI controller when in another guidance state than the third guidance state.

7. The apparatus according to claim 5, wherein the UI controller is arranged to disable display of a subset of the operation substep items on a further level of detail upon display of the corresponding operation substep item associated with the subset of the operation substep items on a further level of detail based on an input from the operator when in the third guidance state.

8. The apparatus according to claim 1, wherein the larger amount of guidance includes more operation step items for an operation step than a lesser amount of guidance.

9. A method of an apparatus for a dialysis process comprising a plurality of operation steps, the method comprising:

representing each of the operation steps as an operation step item being a graphical item suitable to be presented on a display of a user interface ("UI"), wherein each operation step item is selectable by an operator if its corresponding operation step is available;

enabling (i) one or more of said operation step items of operation steps to be displayed through the UI, and (ii) selection among the operation step items through an input device of the UI;

receiving an input from an operator;

selecting, during the dialysis process, an amount of operation guidance information of an operation step item based on the input to be in one of at least a first and a second guidance state, wherein the second guidance state provides a larger amount of guidance than the first guidance state by assigning additional operation guidance information of one or more operation step items selectable from multiple operation steps of the dialysis process, wherein the second guidance state is maintained over multiple operation steps of the dialysis process while the second guidance state is selected, and wherein the operator is enabled to toggle between the guidance states during the dialysis process; and enabling display of a subset of the operation substep items upon display of the corresponding operation step item associated with the subset of the operation substep items based on the input when in the second guidance state, wherein such enabling based on input from the operator overrides any corresponding disabling of the display of the operation substep items by a controller when in the first guidance state, wherein at least one of the operation step items comprises operation substep items that represent operation substeps of the at least one operation step by at least one of operation guidance, parameter setting and status information, and wherein the method includes enabling display of the operation substep items upon display of the corresponding operation step item when in another guidance state than the first guidance state.

10. The method according to claim 9, comprising displaying one or more operation step items of said operation step items recommended to be performed next with an indicator representing the recommendation when in another guidance state than the first guidance state.

11. The method according to claim 9, comprising disabling selection of the first guidance state based on a determined skill level of the operator to be below a threshold.

12. The method according to claim 9, comprising
receiving an input from the operator; and
disabling display of a subset of the operation substep items upon display of the corresponding operation step item associated with the subset of the operation substep items based on the input when in another guidance state than the first guidance state.

13. The method according to claim 9, wherein the at least a first and a second guidance state comprises a third guidance state, wherein the third guidance state provides a larger amount of guidance than the second guidance state over multiple operation steps of the dialysis process, and the operation substep items comprises operation substep items on a further level of detail that represent substeps on a further level of detail of the at least one substep by at least one of operation guidance, parameter setting and status information, and the method comprising enabling display of the operation substep items on a further level of detail upon display of the corresponding operation substep item when in the third guidance state.

14. The method according to claim 13, comprising
receiving an input from the operator; and
enabling display of a subset of the operation substep items on a further level of detail upon display of the corresponding operation substep item associated with the subset of the operation substep items on a further level of detail based on the input from the operator, wherein such enabling based on input from the operator overrides any corresponding disabling of the display of the operation substep items on a further level of detail by a controller when in another guidance state than the third guidance state.

15. The method according to claim 13, comprising
receiving an input from the operator; and
disabling display of a subset of the operation substep items on a further level of detail upon display of the corresponding operation substep item associated with the subset of the operation substep items on a further level of detail based on the input when in the third guidance state.

16. The method according to claim 9, wherein the larger amount of guidance includes more operation step items for an operation step than a lesser amount of guidance.

17. A computer program comprising computer-executable program code which when executed by a processor of the apparatus for the dialysis process causes the apparatus to perform the method according to claim 9.

* * * * *